United States Patent
Gerhart et al.

(10) Patent No.: US 9,968,586 B2
(45) Date of Patent: *May 15, 2018

(54) MAST CELL STABILIZERS TREATMENT FOR SYSTEMIC DISORDERS

(71) Applicant: Patara Pharma, LLC, San Diego, CA (US)

(72) Inventors: William Gerhart, Del Mar, CA (US); Manfred Keller, Munich (DE); Ahmet Tutuncu, Del Mar, CA (US); Pravin Soni, Sunnyvale, CA (US)

(73) Assignee: Patara Pharma, LLC, San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/621,857

(22) Filed: Jun. 13, 2017

(65) Prior Publication Data

US 2017/0273941 A1   Sep. 28, 2017

Related U.S. Application Data

(63) Continuation of application No. 15/232,731, filed on Aug. 9, 2016, now Pat. No. 9,707,206, which is a continuation of application No. PCT/US2015/015029, filed on Feb. 9, 2015.

(60) Provisional application No. 61/937,928, filed on Feb. 10, 2014, provisional application No. 61/971,709, filed on Mar. 28, 2014, provisional application No. 61/978,711, filed on Apr. 11, 2014, provisional application No. 62/105,423, filed on Jan. 20, 2015.

(51) Int. Cl.
| | |
|---|---|
| A61K 31/352 | (2006.01) |
| A61K 47/02 | (2006.01) |
| A61K 9/00 | (2006.01) |
| A61M 11/00 | (2006.01) |
| A61M 15/00 | (2006.01) |
| A61K 9/12 | (2006.01) |
| A61K 47/18 | (2017.01) |
| A61K 31/277 | (2006.01) |
| A61K 31/4422 | (2006.01) |
| A61K 31/4535 | (2006.01) |
| A61K 31/4741 | (2006.01) |
| A61M 11/04 | (2006.01) |
| A61M 11/06 | (2006.01) |

(52) U.S. Cl.
CPC .......... *A61K 31/352* (2013.01); *A61K 9/0075* (2013.01); *A61K 9/0078* (2013.01); *A61K 9/12* (2013.01); *A61K 31/277* (2013.01); *A61K 31/4422* (2013.01); *A61K 31/4535* (2013.01); *A61K 31/4741* (2013.01); *A61K 47/02* (2013.01); *A61K 47/183* (2013.01); *A61M 11/00* (2013.01); *A61M 11/005* (2013.01); *A61M 11/041* (2013.01); *A61M 11/06* (2013.01); *A61M 15/00* (2013.01); *A61M 15/009* (2013.01); *A61M 2202/064* (2013.01)

(58) Field of Classification Search
CPC ................ A61K 31/277; A61K 31/352; A61K 31/4422; A61K 31/4535; A61K 31/4741; A61K 47/02; A61K 47/183; A61K 9/0075; A61K 9/0078; A61K 9/12; A61M 11/00; A61M 11/005; A61M 11/041; A61M 11/06; A61M 15/00; A61M 15/009; A61M 2202/064

See application file for complete search history.

(56) References Cited

U.S. PATENT DOCUMENTS

| | | |
|---|---|---|
| 3,419,578 A | 12/1968 | Fitzmaurice et al. |
| 3,598,122 A | 8/1971 | Zaffaroni |
| 3,683,320 A | 8/1972 | Woods et al. |
| 3,686,320 A | 8/1972 | Fitzmaurice et al. |
| 3,686,412 A | 8/1972 | Fitzmaurice et al. |
| 3,710,795 A | 1/1973 | Higuchi et al. |
| 3,720,690 A | 3/1973 | King et al. |
| 3,731,683 A | 5/1973 | Zaffaroni |
| 3,742,951 A | 7/1973 | Zaffaroni |
| 3,777,033 A | 12/1973 | Fitzmaurice et al. |
| 3,790,580 A | 2/1974 | Johnson et al. |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni et al. |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,067,992 A | 1/1978 | Kingsley et al. |
| 4,069,307 A | 1/1978 | Higuchi et al. |
| 4,077,407 A | 3/1978 | Theeuwes et al. |
| 4,151,273 A | 4/1979 | Riegelman et al. |
| 4,152,448 A | 5/1979 | Wardell |

(Continued)

FOREIGN PATENT DOCUMENTS

| | | |
|---|---|---|
| EP | 0 163 683 A1 | 12/1985 |
| EP | 0 304 802 A2 | 3/1989 |

(Continued)

OTHER PUBLICATIONS

U.S. Appl. No. 62/381,914, filed Aug. 31, 2016, Patara Pharma, LLC.
U.S. Appl. No. 62/405,587, filed Oct. 7, 2016, Patara Pharma, LLC.
U.S. Appl. No. 62/417,887, filed Nov. 4, 2016, Patara Pahrma, LLC.
U.S. Appl. No. 62/417,898, filed Nov. 4, 2016, Patara Pharma, LLC.
Advisory Action for U.S. Appl. No. 14/617,221 dated Aug. 19, 2016.
Afrin, B. Lawrence, "Presentation, Diagnosis, and Management of Mast Cell Activation Syndrome," Mast Cells (2013) Chapter 6.
Allistone, A. et al., The effect of intravenous sodium cromoglycate on the bronchoconstriction induced by sulphur dioxide inhalation in man. Clinical Science, 68:227-232 (1985).
Anderson et al., "Sodium Cromoglycate Alone and in Combination with Montelukast on the Airway Response to Mannitol in Asthmatic Subjects," J Asthma, (2010), 47:429-433.

(Continued)

*Primary Examiner* — Savitha M Rao
(74) *Attorney, Agent, or Firm* — Mintz Levin Cohn Ferris Glovsky and Popeo PC

(57) ABSTRACT

Methods for the treatment of systemic disorders treatable with mast cell stabilizers, including mast cell related disorders, are provided.

22 Claims, No Drawings

(56) References Cited

U.S. PATENT DOCUMENTS

| | | |
|---|---|---|
| 4,189,571 A | 2/1980 | Bodor et al. |
| 4,201,211 A | 5/1980 | Chandrasekaran et al. |
| 4,229,447 A | 10/1980 | Porter |
| 4,230,105 A | 10/1980 | Harwood |
| 4,268,519 A | 5/1981 | Turner |
| 4,292,299 A | 9/1981 | Suzuki et al. |
| 4,292,303 A | 9/1981 | Keith et al. |
| 4,343,789 A | 8/1982 | Kawata et al. |
| 4,362,742 A | 12/1982 | Sullivan |
| 4,476,116 A | 10/1984 | Anik |
| 4,496,086 A | 1/1985 | Duchadeau |
| 4,596,795 A | 6/1986 | Pitha |
| 4,634,699 A | 1/1987 | McDermed et al. |
| 4,683,135 A | 7/1987 | Pecht et al. |
| 4,755,386 A | 7/1988 | Hsiao et al. |
| 4,847,286 A | 7/1989 | Tamaki et al. |
| 4,871,865 A | 10/1989 | Lever, Jr. et al. |
| 4,923,892 A | 5/1990 | Lever, Jr. et al. |
| 4,996,296 A | 2/1991 | Pecht et al. |
| 5,049,389 A | 9/1991 | Radhakrishnan |
| 5,116,817 A | 5/1992 | Anik |
| 5,280,784 A | 1/1994 | Kohler |
| 5,281,420 A | 1/1994 | Kelm et al. |
| 5,309,900 A | 5/1994 | Knoch et al. |
| 5,312,046 A | 5/1994 | Knock et al. |
| 5,336,168 A | 8/1994 | Sibalis |
| 5,340,591 A | 8/1994 | Nakano et al. |
| 5,456,923 A | 10/1995 | Nakamichi et al. |
| 5,458,136 A | 10/1995 | Jaser et al. |
| 5,461,695 A | 10/1995 | Knoch |
| 5,475,023 A | 12/1995 | Baskeyfield et al. |
| 5,508,451 A | 4/1996 | Bhattacharya et al. |
| 5,549,102 A | 8/1996 | Intl et al. |
| 5,552,436 A | 9/1996 | Clemente et al. |
| 5,567,720 A | 10/1996 | Averback |
| 5,576,346 A | 11/1996 | Clemente et al. |
| 5,618,842 A | 4/1997 | Della Valle et al. |
| 5,665,378 A | 9/1997 | Davis et al. |
| 5,700,485 A | 12/1997 | Berde et al. |
| 5,723,269 A | 3/1998 | Akagi et al. |
| 5,739,136 A | 4/1998 | Ellinwood, Jr. et al. |
| 5,740,966 A | 4/1998 | Blaha-Schnabel |
| 5,753,208 A | 5/1998 | Nagy et al. |
| 5,837,280 A | 11/1998 | Kenealy et al. |
| 5,869,090 A | 2/1999 | Rosenbaum |
| 5,957,389 A | 9/1999 | Wunderlich et al. |
| 6,000,394 A | 12/1999 | Blaha-Schnabel et al. |
| 6,004,949 A | 12/1999 | Shima et al. |
| 6,083,518 A | 7/2000 | Lindahl |
| 6,085,741 A | 7/2000 | Becker |
| 6,176,237 B1 | 1/2001 | Wunderlich et al. |
| 6,207,684 B1 | 3/2001 | Aberg |
| 6,225,327 B1 | 5/2001 | Miller |
| 6,365,180 B1 | 4/2002 | Meyer et al. |
| 6,391,452 B1 | 5/2002 | Antonsen et al. |
| 6,475,467 B1 | 11/2002 | Keller et al. |
| 6,503,481 B1 | 1/2003 | Thurston et al. |
| 6,513,519 B2 | 2/2003 | Gallem |
| 6,513,727 B1 | 2/2003 | Jaser et al. |
| 6,596,261 B1 | 7/2003 | Adjei et al. |
| 6,596,284 B1 | 7/2003 | Fleming et al. |
| 6,660,715 B2 | 12/2003 | Klibanov |
| 6,923,983 B2 | 8/2005 | Morgan et al. |
| 6,929,801 B2 | 8/2005 | Klose et al. |
| 6,946,144 B1 | 9/2005 | Jordan |
| 7,060,827 B2 | 6/2006 | Singh et al. |
| 7,074,388 B2 | 7/2006 | Adjei et al. |
| 7,258,872 B1 | 8/2007 | Wigmore |
| 7,550,133 B2 | 6/2009 | Hale et al. |
| 8,006,698 B2 | 8/2011 | Boehm et al. |
| 8,088,935 B2 | 1/2012 | Pearson et al. |
| 8,252,807 B2 | 8/2012 | Logsdon et al. |
| 8,263,645 B2 | 9/2012 | Keller |
| 8,361,509 B2 | 1/2013 | Lopez-Belmonte Encina et al. |
| 8,470,805 B2 | 6/2013 | Chen |
| 8,513,300 B2 | 8/2013 | Abbas et al. |
| 8,586,044 B2 | 11/2013 | Thumbikat et al. |
| 8,617,517 B2 | 12/2013 | Elmaleh et al. |
| 9,198,859 B2 | 12/2015 | Keller et al. |
| 9,265,749 B2 | 2/2016 | Gerhart et al. |
| 9,707,206 B2 | 7/2017 | Gerhart et al. |
| 2002/0009491 A1 | 1/2002 | Rothbard et al. |
| 2004/0013734 A1 | 1/2004 | Babcock et al. |
| 2004/0204399 A1 | 10/2004 | Osbakken et al. |
| 2005/0209141 A1 | 9/2005 | Silver et al. |
| 2005/0244339 A1 | 11/2005 | Jauernig et al. |
| 2007/0036860 A1 | 2/2007 | Wigmore |
| 2007/0086981 A1 | 4/2007 | Meijer et al. |
| 2007/0193577 A1 | 8/2007 | Keller |
| 2008/0032918 A1 | 2/2008 | Silver et al. |
| 2008/0194676 A1 | 8/2008 | Abbas et al. |
| 2008/0214491 A1 | 9/2008 | Logsdon et al. |
| 2009/0081274 A1 | 3/2009 | Silver et al. |
| 2009/0239916 A1 | 9/2009 | Tanaka et al. |
| 2009/0318545 A1 | 12/2009 | Silver et al. |
| 2011/0112183 A1 | 5/2011 | Riggs-Sauthier et al. |
| 2011/0195924 A1 | 8/2011 | Logsdon et al. |
| 2012/0118991 A1 | 5/2012 | Keller et al. |
| 2013/0017247 A1 | 1/2013 | Harish et al. |
| 2014/0140927 A1 | 5/2014 | Elmaleh et al. |
| 2015/0057299 A1 | 2/2015 | Ford et al. |
| 2015/0224077 A1 | 8/2015 | Gerhart et al. |
| 2015/0224078 A1 | 8/2015 | Gerhart et al. |
| 2015/0297557 A1 | 10/2015 | Gerhart et al. |
| 2015/0306107 A1 | 10/2015 | Chen |
| 2015/0337315 A1 | 11/2015 | Grunstein |
| 2016/0263257 A1 | 9/2016 | Elmaleh et al. |
| 2016/0346245 A1 | 12/2016 | Gerhart et al. |
| 2016/0346246 A1 | 12/2016 | Gerhart et al. |
| 2016/0367519 A1 | 12/2016 | Gerhart et al. |
| 2016/0367520 A1 | 12/2016 | Gerhart et al. |

FOREIGN PATENT DOCUMENTS

| | | |
|---|---|---|
| EP | 0 413 583 A2 | 2/1991 |
| EP | 0 413 583 A3 | 7/1991 |
| EP | 0 183 457 | 1/1992 |
| EP | 0 304 802 B1 | 3/1993 |
| EP | 0 587 264 | 3/1994 |
| EP | 0 587 264 B1 | 10/1994 |
| EP | 1 754 492 A1 | 2/2007 |
| EP | 2 248 517 A1 | 11/2010 |
| EP | 2 391 618 A2 | 12/2011 |
| EP | 2 391 618 A4 | 7/2012 |
| EP | 2 248 517 B1 | 3/2014 |
| JP | S61-143318 | 7/1986 |
| JP | H06-072869 | 3/1994 |
| JP | 2012-526084 | 10/2012 |
| WO | WO-85/02541 A1 | 6/1985 |
| WO | WO-95/05816 | 3/1995 |
| WO | WO-96/31204 A1 | 10/1996 |
| WO | WO-96/31205 A1 | 10/1996 |
| WO | WO-98/31346 A1 | 7/1998 |
| WO | WO-00/27392 A1 | 5/2000 |
| WO | WO-00/36915 A1 | 6/2000 |
| WO | WO-00/42993 A2 | 7/2000 |
| WO | WO-03/045331 A2 | 6/2003 |
| WO | WO-2005/037317 A2 | 4/2005 |
| WO | WO-2005/063732 A1 | 7/2005 |
| WO | WO-2005/077189 A1 | 8/2005 |
| WO | WO-2005/115468 A1 | 12/2005 |
| WO | WO-2007/090646 | 8/2007 |
| WO | WO-2009/027095 | 3/2009 |
| WO | WO-2009/045291 A2 | 4/2009 |
| WO | WO-2009/131695 A1 | 10/2009 |
| WO | WO-2010/042504 A1 | 4/2010 |
| WO | WO-2010/088455 A2 | 8/2010 |
| WO | WO-2010/128111 | 11/2010 |
| WO | WO-2010/128111 A1 | 11/2010 |
| WO | WO-2012/031445 A1 | 3/2012 |
| WO | WO-2014/066318 A1 | 5/2014 |
| WO | WO-2014/115098 A1 | 7/2014 |
| WO | WO-2015/002703 A1 | 1/2015 |
| WO | WO-2015/120389 A1 | 8/2015 |

(56) References Cited

FOREIGN PATENT DOCUMENTS

| WO | WO-2015/120392 A1 | 8/2015 |
|---|---|---|
| WO | WO-2015/161510 A1 | 10/2015 |
| WO | WO-2017/011729 A1 | 1/2017 |
| WO | WO-2017/027387 A1 | 2/2017 |
| WO | WO-2017/027402 A1 | 2/2017 |

OTHER PUBLICATIONS

Ariyanayagam, M. et al., Topical sodium cromoglycate in the management of atopic eczema—a controlled trial. British Journal of Dermatology, 112:343-348 (1985).
Ashton, M. J. et al., The absorption, metabolism and excretion of disodium cromoglycate in nine animal studies. Toxicology and Applied Pharmacology, 26:319-328 (1973).
Aswania O. A., et al., Relative bioavailability of sodium cromoglycate to the lung following inhalation, using urinary excretion. British Journal of Clinical Pharmacology, 47:613-618 (1999).
Aswania, et al., "Relative Lung and Systemic Bioavailability of Sodium Cromoglycate Inhaled Products Using Urinary Drug Excretion Post Inhalation," Biopharm. Drug Dispos., (2002), 23:159-163.
Aswania, et al., "Relative Lung Bioavailability of Generic Sodium Cromoglycate Inhalers Used With and Without a Spacer Device," Pulmonary Pharmacology & Therapeutics, (2001), 14:129-133.
Auty, R. M. et al., Respiratory tract deposition of sodium cromoglycate is highly dependent upon technique of inhalation using the spinhaler. British Journal Dis. Chest, 81:371-380 (1987).
Balzar et al., "Mast Cell Phenotype, Location, and Activation in Severe Asthma. Data from the Severe Asthma Research Program," Am J Respir Crit Care Med. (2011)(e-Pub Date Sep. 2, 2010) 183:299-309.
Balzar et al., "Relationships of Small Airway Chymase-Positive Mast Cells and Lung Function in Severe Asthma," Am J Respir Crit Care Med. (2005), 171:431-439.
Barnes, P.J., "New concepts in the pathogenesis of bronchial hyperresponsiveness and asthma," J Allergy Clin Immunol., (1989), 83:1013-1026.
Behr, et al., "Lung Deposition of a Liposomal Cyclosporine A Inhalation Solution in Patients after Lung Transplantation," J Med Pulm Drug Deliv., (2009), 22(2):121-129.
Benson, et al., "Uptake of disodium cromoglycate in obstructive airways disease," Clinical Allergy, (1973), 3:389-394.
Bizzintino et al., "Association between human rhinovirus C and severity of acute asthma in children," Eur REspir J., (2011), 37:1037-1042.
Bourdin et al., "Upper airway • 1:Allergic rhinitis and asthma: united disease through epithelial cells," Thorax, (2009), 64:999-1004.
Brannan, et al., "Inhibition of mast cell PGD2 release protects against mannitol-induced airway narrowing," Eur Respir J., (2206), 27:944-950.
Burgel, et al., "Update on the roles of distal airways in asthma," Eur Respir REv., (2009), 18:80-95.
Chen, H. H, Chronic cough. Medscape Reference. Drugs, Diseases & Procedures. 5 pages, Updated May 13, 2014.
Cho, A., Recent Advances in Oral Prodrug Discovery. Annual Reports in Medicinal Chemistry, vol. 41, 395-407, (2006).
Cieslewicz, et al., "The late, but not early, asthmatic response is dependent on IL-5 and correlates with eosinophil infiltration," J Clin Inv., (1999), 104(3):301-308.
Coates, et al., "Rapid Pulmonary Delivery of Inhaled Tobramycin for Pseudomonas Infection in Cystic Fibrosis: A Pilot Project," Pediatr Pulmonol., (2008), 43:753-759.
Cox, et al., "Solid-State Chemistry of Cromolyn Sodium (Disodium Cromoglycate)," J Pharm Sci., (1971), 60:1458-1465.
Curry et al., "Disposition of Disodium Cromoglycate Administered in Three Particle Sizes," Br J Clin Pharmac., (1975), 2:267-270.
Diaz, et al., "Bronchoalveolar lavage in asthma: The effect of disodium cromoglycate (cromolyn) on leukocyte counts, immunoglobulins, and complement," J Allergy Clin Immunol., (1984), 74:41-48.

Dixon, M. et al., The Action of sodium cromoglycate on "C" fibre endings in the dog lung. Br. J. Pharm., 70:11-13 (1980).
Doenicke, A. et al., Osmolalities of propylene Glycol-Containing Drug Formulations for Parenteral Use. Should Propylene Glycol be used as a Solvent?, Anesth. Analg. 75:431 (5), (1992).
Edwards, A. M. et al., Oral and inhaled sodium cromoglycate in the management of systemic mastocytosis: a case report. Journal of Medical Case Reports, 4:193-198 (2010).
Edwards, et al., "Inhaled sodium cromoglycate in children with asthma," Thorax, (2002), 57:282.
Edwards, et al., "Sodium cromoglycate in childhood asthma," Thorax, (2001), 56:331-332.
Eggleston, P.A., "Exercise-Induces Asthma," Clin Rev Allergy, (1983), 1:19-37.
Emisphere Technologies, Inc., The facts on . . . Oral Cromolyn Sodium. 2 pages. (2006).
Estfan, B. et al., Management of cough in advanced cancer. Journal of Supportive Oncology, 2(6):523-527 (2004).
FDA Guidance for Industry, "Bioavailability and Bioequivalence Studies for Nasal Aerosols and Nasal Sprays for Local Action," Biopharmaceutics, (2003) 37 Pgs.
Final Rejection for U.S. Appl. No. 14/617,221 dated Jun. 16, 2016.
Finlay, W. H. et al., "Recent advances in predictive understanding respiratory tract deposition." Journal of Aerosol Medicine, 21:189-205 (2008).
Fukasawa, et al., "The Effects of Disodium Cromoglycate on Enhanced Adherence of Haemophilus influenzae to A549 Cells Infected With Respiratory Syncytial Virus," Pediatric Research, (2009), 66(2):168-173.
Furukawa, et al., "A Double-Blind Study Comparing the Effectiveness of Cromolyn Sodium and Sustained-Release Theophylline in Childhood Asthma," Pediatrics, (1984), 74(4):453-459.
Furusho, et al., "The combination of nebulized sodium cromoglycate and salbutamol in the treatment of moderate-to-severe asthma in children," Pediatric Allergy Imminol., (2002), 13:209-216.
Hamid et al., "Inflammation of small airways in asthma," J Allergy Clin Immunol., (1997), 100:44-51.
Hargreaves, M. R. et al., Inhaled sodium cromoglycate in angiotensin-converting enzyme inhibitor cough. Lancet, 345:13-16 (1995).
Hashimoto et al., "DSCG Reduces RSV-Induced Illness in RSV-Infected Mice," J Med Virol., (2009) 81:354-361.
Hemmati A.A. et al., "The role of sodium cromolyn in treatment of paraquat-induced pulmonary fibrosis in rat", Pharmacological Research, (2002), 46(3):229-234.
Hidari et al., "In vitro and in vivo Inhibitory Effects of Disodium Cromoglycate on Influenza Virus Infection," Biol Pharm Bull., (2004), 27(6):825-830.
Hiller et al., "Physical Properties, Hygroscopicity and Estimated Pulmonary Retention of Various Therapeutic Aerosols," Chest, (1980), 77:318-321.
Hori, Y et al., FDA approved asthma therapeutic agent impacts amyloid B in the brain in a transgenic model of Alzheimer's disease. The Journal of Biological Chemistry, Affinity Sites, Published online on Dec. 2, 2014 as Manuscript M114.586602.
Hoshino et al., "A comparative study of the effects of ketotifen, disodium cromoglycate; and beclomethasone dipropionate on bronchial mucosa and asthma symptoms in patients with atopic asthma," Respir Med., (1998), 92:942-950.
Hoshino et al., "The effect of inhaled sodium cromoglycate on cellular infiltration into the bronchial mucosa and the expression of adhesion molecules in asthmatics," Eur Respir J., (1997), 10:858-865.
Intal FDA Label "Intal® Nebulizer Solution," Aventis Pharmaceuticals, Inc. (2003) 6 pgs.
Intal Spincaps, Sodium Cromoglicate 20 mg capsules, Feb. 2007, 4 pages.
Ivax Pharmaceuticals, Cromolyn Sodium-Cromolyn sodium inhalation solution prescribing information, accessed at https://dailymed.nlm.nih.gov/dailymed/ drugInfo.cfm?setid=8fe37a7a-edd6-4733-bb7e-eO1c1906aeba May 2, 2016.

(56) References Cited

OTHER PUBLICATIONS

Iyer, V. N. et al., Chronic Cough: An Update. Mayo Clinic Proceedings. 88(10):1115-1126 (2013).
Jones, et al., "Increased Alveolar Epithelial Permeability in Cigarette Smokers," The Lancet, (1980), 1:66-68.
Kano, et al., "Change in osmolarity of disodium cromoglycate solution and protection against exercise-induced bronchospasm in children with asthma," Eur Respir J., (1996), 9:1891-1895.
Kato, Y. et al. Plasma Concentrations of Disodium Cromoglycate After Various Inhalation Methods in Healthy Subjects. British Journal of Clinical Pharmacology. 48(2) 154-157 (1999).
Keller et al., "Importance of the Inhaler System and Relative Humidity on the Fine Particle Dose (FPD) of Disodium Cromoglycate (DSCG)," RDDD Europe, (2007), 307-310.
Keller, M. et al., Did inappropriate delivery systems hamper therapeutic efficacy of Di-Sodium-Cromo-Glycate (DSCG)? Time for a Reappraisal. Poster Presentation. PARI Pharma: ISAM, P-089, 1 page (2011).
Keller, M. et al., Have inadequate delivery systems hampered the clinical success of inhaled disodium cromoglycate? Time for reconsideration. Expert Opin. Drug Delivery, 8(1):1-17 (2011).
Keller, Manfred "Innovations and perspectives of metered dose inhalers in pulmonary drug delivery," Int J Pharma., (1999), 186:81-90.
Kippelen et al., "Effect of Sodium Cromoglycate on Mast Cell Mediators during Hyperpnea in Athletes," Med Sci Sports Exerc., (2010) 1853-1860.
Kohler et al., "Lung deposition after inhalation with various nebulisers in preterm infants," Arch Dis Child Fetal Neonatal., (2008), 93(4):F275-F279.
Kohler, et al., "Does Wearing a Noseclip during Inhalation Improve Lung Deposition?" J. Aerosol Med., (2004), 17(2):116-122.
Kohler, et al., "Lung Deposition in Cystic Fibrosis Patients Using an Ultrasonic or a Jet Nebulizer," JAMA, (2003), 16(1):37-46.
Korppi et al., "Disodium Cromoglycate in Asthma—Worth to Be Re-appraised," Allergol Int., (2008), 57:183.
Krawiec et al., "Inhaled Nonsteroidal Anti-inflammatory Medications in the Treatment of Asthma," Respir Care Clin N Am., (1999), 5(4):555-574.
Küpper T et al., "Cromoglycate, reproterol, or both-what's best for exercise-induced asthma", Sleep and Breathing; International Journal of the Science and Practice of Sleep Medicine, Springer, (2012)e-pub Dec. 2011, 16(4):1229-1235.
Larsson, et al., "Sodium cromoglycate attenuates pulmonary inflammation without influencing bronchial responsiveness in healthy subjects exposed to organic dust," Clin Exp Allergy, (2001), 31:1356-1368.
Latimer, K. M. et al., Inhibition by sodium cromoglycate of bronchoconstriction stimulated by respiratory heat loss: comparison or pressurized aerosol and powder. Thorax, 39:277-281 (1984).
Laube et al., "The efficacy of slow versus faster inhalation of cromolyn sodium in protecting against allergen challenge in patients with asthma," J. Allergy Clin Immunol., (1998), 101:475-483.
Lavinka, P. C. et al., Molecular signaling and targets from itch: lessons for cough. Cough, 9:8, 13 pages (2013).
Leitch, A.G. et al., "Disodium cromoglycate relieves symptoms in symptomatic young smokers. A double blind placebo controlled trial", Allergy, (1984), 39(3):211-215.
Leone-Bay, A. et al., Oral delivery of sodium cromolyn: Preliminary studies in vivo and in vitro. Pharmaceutical Research, 13(2):222(1995).
Lindstrom, M. et al., A Simple Pharmacokinetic Method to Evaluate the Pulmonary Dose in Clinical Practice—Analyses of Inhaled Sodium Cromoglycate. Respiratory Medice. 98(1): 9-16 (2004).
Luque Carla A. et al., "Treatment of ACE Inhibitor-Induced Cough", Pharmacotherapy: The Journal of Human Pharmacology and Drug Therapy, (1999), 19(7):804-810.
Miller, T. A. et al., Histone deacetylase inhibitors. Journal of Medicinal Chemistry. 46(24):5097 (2003).
Miyatake, et al., "The New Role of Disodium Cromoglycate in the Treatment of Adults with Bronchial Asthma," Allergol Intl., (2007), 56:231-239.
Moeller, et. al., "Efficacy of high dose inhaled DSCG on asthma control in young children," European Respiratory Society Annual Meeting (ERS), Berlin, Germany, Oct. 4-8, 2008.
Moon, et al., "Quercetin Inhalation Inhibits the Asthmatic Responses by Exposure to Aerosolized-Ovalbumin in Conscious Guinea-pigs," Arch Pharm Res., (2008), 31(6):771-778.
Moroni, M. et al., Inhaled sodium cromoglycate to treat cough in advanced lung cancer patients. British Journal of Cancer, 74:309-311 (1996).
Morrison-Smith et al., "Observations on the safety of disodium cromoglycate in long-term use in children," Clinical Allergy, (1972), 2:143-151.
Moss, G. F. et al., Distribution and metabolism of disodium cromoglycate in rats. Toxicology and Applied Pharmacology, 17:691-698 (1970).
Moss, G. F. et al., Plasma levels and urinary excretion of disodium cromoglycate after inhalation by human volunteers. Toicolocy and Applied Pharmacology, 20:147-156 (1971).
NasalCrom FDA Label 2013.
Neale, M. G. et al., The Pharmacokinetics of sodium cromoglycate in man after intravenous and inhalation administration. British Journal of Clinical Pharm., 22:373-382 (1986).
Nerbrink et al., "Inhalation and Deposition of Nebulized Sodium Cromoglycate in Two Different Particle Size Distributions in Children With Asthma," Pediatr Pulmonol., (2002), 34(5):351-360.
Nogrady. Chapter 4: Pro Drugs and Soft Drugs. In: Medicinal Chemistry: A Biochemical approach. New York: Oxford Universitry Press, p. 388-392 (1985).
Non-final Office action for U.S. Appl. No. 14/617,130 dated May 9, 2016.
Northern General Hospital, Brompton Hospital, "Sodium cromoglycate in chronic asthma," Br. Med. J., (1976), 1:361-364.
Patel, et al., "Dose-response study of sodium cromoglycate in exercise0induces asthma," (1982), 37:663-666.
Patel, et al., "The dose-duration effect of sodium cromoglycate in exercise-induced asthma," Clin Allergy, (1984), 14:87-91.
Patel, K. R. et al., Plasma concentrations of sodium cromoglycate given by nebulisation and metered dose inhalers in patients with exercise-induced asthma: relationship to protective effect. Br. J. Clin. Pharmac., 21:231-233 (1986).
PCT/US2015/015029 International Search Report and Written Opinion dated Aug. 13, 2015.
PCT/US2015/015033 International Search Report and Written Opinion dated Aug. 13, 2015.
PCT/US2016/042437 International Search Report and Written Opinion dated Jan. 19, 2017.
PCT/US2016/045804 International Search Report and Written Opinion dated Feb. 16, 2017.
PCT/US2016/045849 International Search Report and Written Opinion dated Feb. 16, 2017.
Penttinen, et al., "Disodium cromoglycate can inhibit virus-induced cytopathic effects in vitro," Br Med J., (1977), 1:182.
Picard, M. et al., Expanding spectrum of mast cell activation disorders: Monoclonal and idiopathic mast cell activation syndromes. Clinical Therapeutics, 35(5): 548 (2013).
Reijonen, et al., "Anti-inflammatory Therapy Reduces Wheezing After Bronchiolitis," Arch Pediatr Adolesc Med., (1996), 150:512-517.
Riccardi, V. M., Cutaneous manifestation of neurofibromatosis: cellular interaction, pigmentation, and mast cells, Birth Defects Org Artie Ser, 17: 129-45 (1981) (Abstract only).
Richards, et al., Absorption and disposition kinetics of cromolyn sodium and the influence of inhalation technique. Journal of Pharmacology and Experimental Therapeutics, 241(3): 1028-1032 (1987).
Richards, R. et al., Deep inspiration increases the absorption of inhaled sodium cromoglycate. Br. J. Clin. Pharmac., 27:861-865 (1989).
Richards, R. et al., Effect of methacholine induced bronchoconstriction on the pulmonary distribution and plasma pharmacokinetics of

(56) References Cited

OTHER PUBLICATIONS inhaled sodium cromoglycate in subjects with normal and hyper-reactive airways. Thorax. 43:611-616 (1988).
Richards, R. et al., Inhalation rate of sodium cromoglycate determines plasma pharmacokinetics and protection against AMP-induced bronchoconstriction in asthma. Eu.Respir. J., 1:896-901 (1988).
Richards, R. et al., Inhaled histamine increases the rate of absorption of sodium cromoglycate from the lung. Br. J. Clin. Pharma, 33:337-341 (1992).
Robuschi, M. et al., "Attenuation of aspirin-induced bronchoconstriction by sodium cromoglycate and nedocromil sodium", American Journal of Respiratory and Critical Care Medicine, American Lung Association, New York, NY, (1997), 155(4):1461-1464.
Rooseboom, M. et al., Enzyme-catalyzed activation of anticancer prodrugs. Pharmacological Reviews, 56(1):53-102 (2004).
Salmon, B. et al., How much aerosol reaches the lungs of wheezy infants and toddlers? Archives of Disease in Childhood, 65:401-403 (1990).
Saulnier, M. G. et al. An efficient method for the synthesis of guanidino prodrugs. Bioorganic &Medicinal Chemistry Letters. 4(16):1985-1990 (1994).
Shenfield, et al., "Absorption of drugs by the Lung," Br. J Clin Pharmac., (1976), 3:583-589.
Silverman, M., "Inhaled sodium cromoglycate," Thorax, (2001), 56:585-586.
Silverman, R. B. et al. Chapter 8: Prodrugs and drug delivery systems. In: The Organic Chemistry of Drug Design and Drug Action. San Diego: Academic Press, Inc. p. 352-401 (1992).
Soferman, et al., "Comparison between bronchial response to inhaled hypoosmolar and isoosmolar solutions of sodium cromoglycate after exercise challenge," Annals of Allergy, (1990), 64:143-146.
Stevens, et al., "Sodium cromoglicate: an ineffective drug or meta-analysis misused?" Pharm Stat., (2007), 6:123-137.
Storms, et al., "Cromolyn Sodium: Fitting an Old Friend into Current Asthma Treatment," J Asthma, (2005), 42:79-89.
Tang, et al., "Aerosol Growth Studies III.," J Aerosol Sci., (1977), 8:321-330.
Tasche et al., "Inhaled disodium cromoglycate (DSCG) as maintenance therapy in children with asthma: a systematic review," Thorax, (2000), 55:913-920.
Taylor, et al., "Estimation of equivalent pore radii of pulmonary capillary and alveolar membranes," Am J Physiocol., (1970), 218:1133-1140.
Taylor, K. M. G. et al., The Influence of Liposomal encapsulation on sodium cromoglycate pharmacokinetics in man. Pharmaceutical Research, 6(7):633-636 (1989).
Tulic, et al., "Contribution of the Distal Lung to the Pathologic and Physiologic Changes in Asthma," Chest, (2003), 123:348S-355S.
Tullett et al., "Dose-response effect of sodium cromoglycate pressurised aerosol in exercise induced asthma," Thorax, (1985), 40:41-44.
U.S. Appl. No. 14/617,221 Office Action dated Aug. 26, 2015.
U.S. Appl. No. 14/686,535 Notice of Allowance dated Jan. 5, 2016.
U.S. Appl. No. 14/686,535 Office Action dated Jun. 25, 2015.
Urbano, et al., "Review of the NAEPP 2007 Expert Panel Report (EPR-3) on Asthma Diagnosis and Treatment Guidelines," JMCP, (2008), 14(1):41-49.
US Notice of Allowance dated Mar. 23, 2017 for U.S. Appl. No. 15/232,731.
US Notice of Allowance dated Mar. 29, 2017 for U.S. Appl. No. 15/232,731.
US Office Action dated Apr. 6, 2017 in U.S. Appl. No. 15/117,711.
US Office Action dated Nov. 15, 2016 in U.S. Appl. No. 15/232,731.
US Office Action dated Jan. 11, 2017 in U.S. Appl. No. 14/617,130.
US Office Action dated Dec. 2, 2016 in U.S. Appl. No. 15/232,747.
Van De Wouden et al., "Sodium Cromoglycate for Asthma in Children(Review)," Cochran Database Syst Rev., (2003), 1-48.
Van De Wouden, et al., "Inhaled sodium cromoglycate for asthma in children (Review)," Cochrane Library, (2011), 3:1-69.
Vessal, G. et al., Effect of oral cromolyn sodium on CKD-associated pruritus and serum tryptase level: a double-blind placebo-controlled study. Nephrol Dial Transplant. 25:1541-1547 (2010).
Walker, S. R. et al., The Fate of [14C]disodium Cromoglycate in Man, J. Pharm. Pharmacol., 24:525-531 (1972).
Weiner et al., "Isotonic Nebulized Disodium Cromoglycate Provides Better Protection against Methacholine- and Exercise-induced Bronchoconstriction," Am Rev Respir Dis., (1988), 137:1309-1311.
Yahav, Y. et al., Sodium cromoglycate in asthma: correlation between response and serum concentrations. Archives of Disease in Childhood. 63:592-597 (1988).
Yamazaki, et al., "The Inhibitory Effect of Disodium Cromoglycate on the Growth of Chlamydophila (Chlamydia) pneumoniae in vitro," Biol Pharm Bull., (2006), 29(4):799-800.
Yoshimi, A. et al., Characteristics of 1,3-Bis-(2-ethoxycarbonylchromon-5-yloxy)-2-((S)-lysyloxy)propane Dihydrochloride (N-556), a Prodrug for the oral delivery of disodium cromoglycate, in absorption and excretion in rats and rabbits. J.Pharmacobio-Dyn., 15:681-686 (1992).
Yoshimi, A. et al., Importance of hydrolysis of amino acid moiety in water-soluble prodrugs of disodium cromoglycate for increased orral bioavailability. J.Pharmacobio-Dyn., 15:339-345 (1992).
Horan et al., "Cromolyn sodium in the management of systemic mastocytosis", J. Allergy Clin. Immunol., 1990, pp. 852-855.
US Office Action for U.S. Appl. No. 15/232,747 dated Jun. 21, 2017. (36 pages).
Asmus et al., "Pulmonary function response to EDTA, an additive in nebulized bronchodilators", Journal of Allergy and Clinical Immunology, 2001, 107(1):68-72.
Monk, K.R., "Thesis: Consequences of Mast Cell Signaling in Peripheral Nerve", University of Cincinnati, 2006, downloaded from https://etd.ohiolink.edu/rws_etd/document/get/ucin1147889736/inline Oct. 17, 2017.
Spooner et al., "Mast-cell stabilising agents to prevent exercise-induced bronchoconstriction", Copyright @ 2009 The Cochrane Collaboration, Article first published online: Oct. 20, 2003, pp. 1-40.
US Office Action for U.S. Appl. No. 14/617,221 dated Oct. 25, 2017. (50 Pages).
Zamora et al., "Neurofibromatosis-associated lung disease: a case series and literature review", European Respiratory Journal, 2007, 29:210-214.
US Office Action for U.S. Appl. No. 15/117,711 dated Oct. 3, 2017. (26 pages).
PCT International Search Report and Written Opinion for Application No. PCT/US2017/049205 dated Nov. 3, 2017. (16 pages).
"View of NCT02412020 on Apr. 7, 2015." *NCT02412020 on Apr. 7, 2015: ClinicalTrials.Gov Archive*, Accessed Jan. 30, 2018. clinicaltrials.gov/archive/NCT02412020/2015_04_07.
"View of NCT02412020 on Apr. 8, 2015." *NCT02412020 on Apr. 8, 2015: ClinicalTrials.Gov Archive*, Accessed Jan. 30, 2018. clinicaltrials.gov/archive/NCT02412020/2015_04_08.
"View of NCT02412020 on Sep. 25, 2015." *NCT02412020 on Sep. 25, 2015: ClinicalTrials.Gov Archive*, Accessed Jan. 30, 2018. clinicaltrials.gov/archive/NCT02412020/2015_09_25.
"View of NCT02412020 on Feb. 19, 2016." *NCT02412020 on Feb. 19, 2016: ClinicalTrials.Gov Archive*, Accessed Jan. 30, 2018. clinicaltrials.gov/archive/NCT02412020/2016_02_19.
"View of NCT02478957 on Jun. 22, 2015." *NCT02478957 on Jun. 22, 2015: ClinicalTrials.Gov Archive*, Accessed Jan. 30, 2018. clinicaltrials.gov/archive/NCT02478957/2015_06_22.
"View of NCT02478957 on Sep. 25, 2015." *NCT02478957 on Sep. 25, 2015: ClinicalTrials.Gov Archive*, Accessed Jan. 30, 2018. clinicaltrials.gov/archive/NCT02478957/2015_09_25.
"View of NCT02478957 on Feb. 26, 2016." *NCT02478957 on Feb. 26, 2016: ClinicalTrials.Gov Archive*, Accessed Jan. 30, 2018. clinicaltrials.gov/archive/NCT02478957/2016_02_26.
"View of NCT02478957 on Sep. 28, 2016." *NCT02478957 on Sep. 28, 2016: ClinicalTrials.Gov Archive*, Accessed Jan. 30, 2018. clinicaltrials.gov/archive/NCT02478957/2016_09_28.

(56) References Cited

OTHER PUBLICATIONS

"View of NCT02696499 on Mar. 1, 2016." *NCT02696499 on Mar. 1, 2016: ClinicalTrials.Gov Archive*, Accessed Jan. 30, 2018. clinicaltrials.gov/archive/NCT02696499/2016_03_01.

"View of NCT02696499 on May 3, 2016." *NCT02696499 on May 3, 2016: ClinicalTrials.Gov Archive*, Accessed Jan. 30, 2018. clinicaltrials.gov/archive/NCT02696499/2016_05_03.

"View of NCT02696499 on Apr. 5, 2017." *NCT02696499 on Apr. 5, 2017: ClinicalTrials.Gov Archive*, Accessed Jan. 30, 2018. clinicaltrials.gov/archive/NCT02696499/2017_04_05.

Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 11, 2014. Accessed Jan. 30, 2018. [online] Available at: https://www.clinicaltrialsregister.eu/ctr-search/trial/2014-004113-85/DE.

Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 22, 2014. Accessed Jan. 30, 2018.[online] Available at: https://www.clinicaltrialsregister.eu/ctr-search/trial/2014-004113-85/ES.

Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 4, 2014. Accessed Jan. 30, 2018.[online] Available at: https://www.clinicaltrialsregister.eu/ctr-search/trial/2014-004113-85/NL.

Clinicaltrialsregister.eu. "Treatment of Chronic Cough with PA101," Clinical Trials Register. Dec. 11, 2014. Accessed Jan. 30, 2018. [online] Available at: https://www.clinicaltrialsregister.eu/ctr-search/trial/2014-004025-40/NL.

Clinicaltrialsregister.eu. "Treatment of Chronic Cough with PA101," Clinical Trials Register. Jan. 6, 2015. Accessed Jan. 30, 2018. [online] Available at: https://www.clinicaltrialsregister.eu/ctr-search/trial/2014-004025-40/GB.

Clinicaltrialsregister.eu. "Treatment of Uremic Pruritus with Inhaled PA101B in Patients with End-Stage Renal Disease Requiring Hemodialysis," Clinincal Trials Register. Jan. 13, 2016. Accessed Jan. 30, 2018. [online] Available at: https://www.clinicaltrialsregister.eu/ctr-search/trial/2015-004794-33/PL.

MAST CELL STABILIZERS TREATMENT FOR SYSTEMIC DISORDERS

CROSS REFERENCE

This application is a continuation application of U.S. patent application Ser. No. 15/232,731, filed on Aug. 9, 2016, which is a continuation application of International Application No. PCT/Us2015/015029, filed Feb. 9,2015; which claims the priority benefit of U.S. Provisional Application No. 61/937,928, filed Feb. 10, 2014; U.S. Provisional Application No. 61/971,709, filed Mar. 28, 2014; U.S. Provisional Application No. 61/978,711, filed Apr. 11, 2014; and U.S. Provisional Application No. 62/105,423, filed Jan. 20, 2015, all of which are incorporated by reference herein in their entireties.

BACKGROUND OF THE INVENTION

Mast cells play a key role in the inflammatory process. They are found in the perivascular spaces of most tissues and contain pro-inflammatory and vasoactive mediators, such as serine proteases, tryptase, histamine, serotonin, proteoglycans, thromboxane, prostaglandin D2, leukotriene C4, platelet-activating factor, and eosinophil chemotactic factor. When activated, mast cells rapidly release granules and various hormone mediators into the interstitium, a process referred to as degranulation. Degranulation of mast cells can be caused by physical or chemical injury, crosslinking of immunoglobulin G receptors, or by activated complement proteins.

Systemic mast cell related disorders may result from excessive proliferation of mast cells or abnormal release of pro-inflammatory and vasoactive mediators. Symptoms of systemic mast cell related disorders include pruritus, flushing, nausea, vomiting, diarrhea, headaches, abdominal pain, vascular instability, urticaria, itching, and anaphylaxis. Accumulation of mast cells in the skin, gastrointestinal tract, bone marrow, liver, spleen, and lymph nodes may result in a particular systemic mast cell related disorder, systemic mastocytosis, or mastocytosis.

The utility of mast cell stabilizers in the treatment of systemic mast cell related disorders, such as mastocytosis, has been limited. For example, cromolyn sodium (also known as disodium cromoglycate or DSCG) was first approved in 1973 and is widely considered safe, but it has found limited utility because the amount of the compound that can be delivered systemically is inadequate. An oral solution of cromolyn sodium is available for the treatment of systemic mast cell related disorders, such as mastocytosis (Gastrocrom®). However, the oral solution is only modestly effective for treating localized gastrointestinal symptoms, and it is not effective for the treatment of systemic symptoms because of the low oral bioavailability of cromolyn sodium (less than 1%).

Efforts have been made to increase the oral bioavailability of cromolyn sodium in order to provide systemically effective amounts for the treatment of systemic mast cell related disorders, but these efforts have not yielded products that achieve significantly higher oral bioavailability of cromolyn sodium in a practical, safe, and well-tolerated manner. Accordingly, a need exists for methods of delivering mast cell stabilizers, such as cromolyn sodium, that achieve higher systemic levels than previously considered or thought possible, in a practical, safe, and well-tolerated manner, in order to significantly improve clinical outcomes for patients suffering from systemic mast cell related disorders.

SUMMARY OF THE INVENTION

The foregoing and further needs are satisfied by embodiments of the methods disclosed herein. Specifically, disclosed herein are methods of treating a systemic mast cell related disorder by delivering a systemically effective amount of a mast cell stabilizer to a patient. In certain embodiments, the systemic mast cell related disorder is selected from the group consisting of a mast cell activation syndrome; mastocytosis; idiopathic urticaria; chronic urticaria; atopic dermatitis; idiopathic anaphylaxis; Ig-E and non Ig-E mediated anaphylaxis; angioedema; allergic disorders; irritable bowel syndrome; mastocytic gastroenteritis; mastocytic colitis; fibromyalgia; kidney fibrosis; atherosclerosis; myocardial ischemia; hypertension; congestive heart failure; pruritus; chronic pruritus; pruritus secondary to chronic kidney failure; heart, vascular, intestinal, brain, kidney, liver, pancreas, muscle, bone and skin conditions associated with mast cells; CNS diseases such as Parkinson's disease and Alzheimer's disease; metabolic diseases such as diabetes; sickle cell disease; autism; chronic fatigue syndrome; lupus; chronic lyme disease; interstitial cystitis; multiple sclerosis; cancer; migraine headaches; psoriasis; eosinophilic esophagitis; eosinophilic gastroenteritis; Churg-Strauss syndrome; hypereosinophilic syndrome; eosinophilic fasciitis; eosinophilic gastrointestinal disorders; chronic idiopathic urticaria; myocarditis; Hirschsprung's-associated enterocolitis; postoperative ileus; wound healing; stroke; transient ischemic attack; pain; neuralgia; peripheral neuropathy; acute coronary syndromes; pancreatitis; cutaneous mastocytosis; systemic mastocytosis; systemic indolent mastocytosis; dermatomyositis; fibrotic skin diseases; pain associated with cancer; ulcerative colitis; inflammatory bowel disease; radiation colitis; celiac disease; gluten enteropathy; radiation cystitis; painful bladder syndrome; hepatitis; hepatic fibrosis; cirrhosis; rheumatoid arthritis; lupus erythematosus; and vasculitis. In some embodiments, administration of a composition disclosed herein in a method disclosed herein is well-tolerated by the patient. In some embodiments, the mast cell stabilizer is selected from cromolyn sodium, cromolyn lysinate, ammonium cromoglycate, magnesium cromoglycate, dihydropyridines such as nicardipine and nifedipine, lodoxamide, nedocromil, barnidipine, YC-114, elgodipine, niguldipine, ketotifen, methylxanthines, and quercetin. In some embodiments, administration of a composition disclosed herein in a method disclosed herein does not cause one or more adverse events selected from the group consisting of oropharyngeal pain, dysgeusia, nasopharygitis, and abdominal discomfort.

In some embodiments, the methods disclosed herein comprise administering a composition comprising a mast cell stabilizer to a patient having a systemic mast cell related disorder, wherein the bioavailability of the mast cell stabilizer is greater than about 5%, and wherein administration of the composition produces in a human subject group an average $AUC_{(0-\infty)}$ of the mast cell stabilizer greater than about 120 ng*hr/mL and/or an average $C_{max}$ of the mast cell stabilizer greater than about 55 ng/mL. In some embodiments of the methods disclosed herein, the composition is administered by a route selected from inhalation administration, oral administration, parenteral administration, subcutaneous administration, topical administration, buccal administration, nasal administration, rectal administration, vaginal administration, and sublingual administration. In some embodiments, the composition is administered with a dry powder inhaler, metered dose inhaler, nebulizer, soft mist inhaler, or high efficiency nebulizer. In some embodiments wherein the composition is administered with a dry powder inhaler, the composition comprises lactose. In some embodiments wherein the composition is administered with a dry powder inhaler, the composition does not comprise lactose. In some embodiments, a composition comprising a mast cell stabilizer is administered once a day. In some embodiments, a composition comprising a mast cell stabilizer is administered twice a day. In some embodiments, a composition comprising a mast cell stabilizer is administered three times a day. In some embodiments, a composition comprising a mast cell stabilizer is administered four times a day. In some embodiments, the composition comprises about 1 mg to about 120 mg of cromolyn sodium. In some embodiments, the composition comprises about 5 mg to about 80 mg of cromolyn sodium. In some embodiments, the composition comprises about 20 mg to about 60 mg of cromolyn sodium. In some embodiments, the composition comprises about 30 mg to about 50 mg of cromolyn sodium. In some embodiments, the composition comprises about 40 mg of cromolyn sodium.

In some embodiments, disclosed herein is a method of treating a patient having a systemic mast cell related disorder comprising administering to the patient a composition comprising a nominal dose of a mast cell stabilizer with a high efficiency nebulizer, wherein administration of the composition to the patient with a high efficiency nebulizer provides a systemically effective amount of the mast cell stabilizer to treat the systemic mast cell related disorder. In certain embodiments, the bioavailability of the mast cell stabilizer is greater than about 5% of the nominal dose administered with the high efficiency nebulizer. In certain embodiments, administration of the composition comprising a mast cell stabilizer with a high efficiency nebulizer produces in a human subject group an average $AUC_{(0-\infty)}$ of the mast cell stabilizer greater than about 120 ng*hr/mL and/or an average $C_{max}$ of the mast cell stabilizer greater than about 55 ng/mL. In certain embodiments, administration of the composition comprising a mast cell stabilizer with a high efficiency nebulizer produces in a human subject group an average $AUC_{(0-\infty)}$ of the mast cell stabilizer greater than about 120 ng*hr/mL and an average $C_{max}$ of the mast cell stabilizer greater than about 55 ng/mL. In certain embodiments, the composition comprising a mast cell stabilizer comprises a high concentration, hypotonic, room temperature stable solution formulation of the mast cell stabilizer. In certain embodiments, the composition is stable at room temperature for more than about two years. In some embodiments, the composition comprises one or more of purified water, sodium chloride, mannitol, and sodium EDTA. In some embodiments, the composition has an osmolality greater than about 70 mOsm/kg. In some embodiments, the composition has a fill volume of about 0.1 mL to about 5 mL. In some embodiments, the composition has a fill volume of about 2 mL or less. In some embodiments, the composition is administered in less than about five minutes. In some embodiments, the composition is administered in less than about three minutes. In some embodiments, the high efficiency nebulizer emits droplets having an MMAD of about 4.1 µm or less and a GSD of about 1.7. In some embodiments, the high efficiency nebulizer emits droplets having an MMAD of about 3.5 µm or less and a GSD of about 1.7. In some embodiments, the RF (≤3.3 µm) is at least about 30% and/or the RF (≤5 µm) is at least about 65%. In some embodiments, the RF (≤3.3 µm) is at least about 45% and/or the RF (≤5 µm) is at least about 75%.

In some embodiments, the mast cell stabilizer is cromolyn sodium. In some embodiments, the deposited lung dose of cromolyn sodium is at least about 25% after administration of the composition to the patient with a high efficiency nebulizer. In some embodiments, administration of the composition with a high efficiency nebulizer produces in a human subject group an average $AUC_{(0-\infty)}$ of the cromolyn sodium greater than about 120 ng*hr/mL, an average $C_{max}$ of the cromolyn sodium greater than about 55 ng/mL, and a deposited lung dose of cromolyn sodium at least about 25%. In some embodiments, the composition comprises greater than about 2% cromolyn sodium. In some embodiments, the composition comprises about 4% cromolyn sodium. In some embodiments, the median particle size of the cromolyn sodium aerosol is between about 3 µm and about 4 µm.

In certain embodiments of the methods disclosed herein, a composition comprising a mast cell stabilizer is administered with an inhalation device, wherein administration of the composition with the inhalation device produces in a human subject group an average $AUC_{(0-\infty)}$ of the mast cell stabilizer greater than about 120 ng*hr/mL and/or an average $C_{max}$ of the mast cell stabilizer greater than about 55 ng/mL. In some embodiments the mast cell stabilizer is cromolyn sodium, and administration of the composition with an inhalation device produces in a human subject group an average $AUC_{(0-\infty)}$ of the cromolyn sodium greater than about 120 ng*hr/mL and an average $C_{max}$ of the cromolyn sodium greater than about 55 ng/mL. In some embodiments the mast cell stabilizer is cromolyn sodium, and administration of the composition with an inhalation device produces in a human subject group an average $AUC_{(0-\infty)}$ of the cromolyn sodium greater than about 200 ng*hr/mL and an average $C_{max}$ of the cromolyn sodium greater than about 80 ng/mL. In some embodiments the mast cell stabilizer is cromolyn sodium, and administration of the composition with an inhalation device produces in a human subject group an average $AUC_{(0-\infty)}$ of the cromolyn sodium greater than about 330 ng*hr/mL and an average $C_{max}$ of the cromolyn sodium greater than about 150 ng/mL. In some embodiments the mast cell stabilizer is cromolyn sodium, and administration of the composition with an inhalation device produces in a human subject group an average $AUC_{(0-\infty)}$ of the cromolyn sodium greater than about 525 ng*hr/mL and an average $C_{max}$ of the cromolyn sodium greater than about 230 ng/mL. In some embodiments wherein the mast cell stabilizer is cromolyn sodium and a nominal dose of 40 mg of cromolyn sodium is administered with the inhalation device, administration of the composition with the inhalation device produces in a human subject group an average $AUC_{(0-\infty)}$ of the cromolyn sodium greater than about 200 ng*hr/mL and an average $C_{max}$ of the cromolyn sodium greater than about 80 ng/mL. In some embodiments wherein the mast cell stabilizer is cromolyn sodium and a nominal dose of 40 mg of cromolyn sodium is administered with the inhalation device, administration of the composition with the inhalation device produces in a human subject group an average $AUC_{(0-\infty)}$ of the cromolyn sodium greater than about 330 ng*hr/mL and an average $C_{max}$ of the cromolyn sodium greater than about 150 ng/mL. In some embodiments wherein the mast cell stabilizer is cromolyn sodium and a nominal dose of 80 mg of cromolyn sodium is administered with the inhalation device, administration of the composition with the inhalation device produces in a human subject group an average $AUC_{(0-\infty)}$ of the cromolyn sodium greater than about 525 ng*hr/mL and an average $C_{max}$ of the cromolyn sodium greater than about 230 ng/mL. In some embodiments wherein the mast cell stabilizer is cromolyn sodium, administration of a composition with an inhalation device provides a bioavailability of the mast cell stabilizer greater than about 5% and produces in a human subject group an average $AUC_{(0-\infty)}$ of cromolyn sodium greater than about 120 ng*hr/mL. In some embodiments wherein the mast cell stabilizer is cromolyn sodium, administration of a composition with an inhalation device provides a bioavailability of cromolyn sodium greater than about 5% and produces in a human subject group an average $AUC_{(0-\infty)}$ of cromolyn sodium greater than about 200 ng*hr/mL. In some embodiments wherein the mast cell stabilizer is cromolyn sodium, administration of a composition with an inhalation device provides a bioavailability of the mast cell stabilizer greater than about 5% and produces in a human subject group an average $AUC_{(0-\infty)}$ of cromolyn sodium greater than about 330 ng*hr/mL. In some embodiments wherein the mast cell stabilizer is cromolyn sodium, administration of a composition with an inhalation device provides a bioavailability of the mast cell stabilizer greater than about 5% and produces in a human subject group an average $AUC_{(0-\infty)}$ of cromolyn sodium greater than about 525 ng*hr/mL. In some embodiments wherein the mast cell stabilizer is cromolyn sodium, administration of a composition with an inhalation device produces in a human subject group an average $AUC_{(0-\infty)}$ of cromolyn sodium greater than about 120 ng*hr/mL, and the composition has an RF (≤3.3 μm) of at least about 30%. In some embodiments wherein the mast cell stabilizer is cromolyn sodium, administration of a composition with an inhalation device produces in a human subject group an average $AUC_{(0-\infty)}$ of cromolyn sodium greater than about 200 ng*hr/mL, and the composition has an RF (≤3.3 μm) of at least about 30%. In some embodiments wherein the mast cell stabilizer is cromolyn sodium, administration of a composition with an inhalation device produces in a human subject group an average $AUC_{(0-\infty)}$ of cromolyn sodium greater than about 330 ng*hr/mL, and the composition has an RF (≤3.3 μm) of at least about 40%. In some embodiments wherein the mast cell stabilizer is cromolyn sodium, administration of a composition with an inhalation device produces in a human subject group an average $AUC_{(0-\infty)}$ of cromolyn sodium greater than about 525 ng*hr/mL, and the composition has an RF (≤3.3 μm) of at least about 40%. In some embodiments the composition administered with an inhalation device is not co-administered with an oral formulation of cromolyn sodium.

DETAILED DESCRIPTION OF THE INVENTION

Unless defined otherwise, all technical and scientific terms used herein have the same meaning as commonly understood by one of skill in the art to which the inventions described herein belong. All publications, patents, and patent applications mentioned in this specification are hereby incorporated by reference to the same extent as if each individual publication, patent, or patent application was specifically and individually indicated to be incorporated by reference.

Definition of Terms

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, are also effective and safe.

As used herein, the terms "comprising," "including," "such as," and "for example" (or "e.g.") are used in their open, non-limiting sense.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the invention.

"Nominal dose," as used herein, refers to the loaded dose, which is the amount of mast cell stabilizer in an inhalation device prior to administration to the patient. The volume of solution containing the nominal dose is referred to as the "fill volume."

"$AUC_{last}$," as used herein refers to the area under the curve from time zero to time of last measurable concentration of active pharmaceutical ingredient (API).

"$AUC_{last}^{HEN}$" as used herein refers to the area under a blood plasma concentration curve up to the last time point for the nominal dose of active pharmaceutical ingredient (API) administered with a high efficiency nebulizer.

"$AUC_{last}^{Conv}$" as used herein refers to the area under a blood plasma concentration curve up to the last time point for a nominal dose of active pharmaceutical ingredient (API) administered with a conventional inhalation device.

"$AUC_{(0-\infty)}$," as used herein refers to the total area under a blood plasma concentration curve for an active pharmaceutical ingredient (API).

"$AUC_{(0-\infty)}^{HEN}$" as used herein refers to the total area under a blood plasma concentration curve for a nominal dose of active pharmaceutical ingredient (API) administered with a high efficiency nebulizer.

"$AUC_{(0-\infty)}^{Conv}$" as used herein refers to the total area under a blood plasma concentration curve for a nominal dose of active pharmaceutical ingredient (API) administered with a conventional inhalation device.

$AUC_{(0-\infty)}$ can be determined by methods known to those of skill in the art. For example, the $AUC_{(0-\infty)}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by liquid chromatography-tandem mass spectrometry (LC-MS/MS), plotting the concentration of API in each sample versus the time of collection after administration, and calculating the area under the curve.

"Substantially the same nominal dose" as used herein means that a first nominal dose of an active pharmaceutical ingredient (API) contains approximately the same number of millimoles of the mast cell stabilizer as a second nominal dose of the mast cell stabilizer.

"Bioavailability" as used herein refers to the amount of unchanged API that reaches the systemic circulation, expressed as a percentage of the dosage of the API that is administered to a subject. By definition, the bioavailability of an intravenous solution containing the active pharmaceutical ingredient (API) is 100%. The bioavailability of an API can be determined by methods known to those of skill in the art. For example, the bioavailability of an API can be determined by collecting urine samples from a subject at various time points following administration of the API to the subject, extracting the API from the urine samples, e.g., by solid-phase extraction, quantifying the amount of the API in each urine sample, adjusting the amount of API collected from the urine by a factor based on the amount of API reaching systemic circulation that is excreted in the urine, and calculating the percentage of the API administered to the subject that reaches the systemic circulation of the subject. In a specific embodiment, the bioavailability of cromolyn sodium can be determined as described in Walker et al., 24 J. Pharm. Pharmacol. 525-31 (1972). In the case of cromolyn sodium, the amount of the compound isolated from the urine is multiplied by two to calculate the total amount reaching systemic circulation after administration because the compound is known to be excreted unmetabolized in equal parts in the urine and feces, i.e., approximately 50% of the amount of cromolyn sodium that reaches systemic circulation is excreted in the urine and approximately 50% of the amount of cromolyn sodium that reaches systemic circulation is excreted in the feces.

"Enhanced lung deposition" as used herein refers to an increase in drug deposition (deposited lung dose) arising out of, for example, improved efficiency of drug delivery.

"Deposited dose" or "deposited lung dose" is the amount of mast cell stabilizer deposited in the lung. The deposited dose or deposited lung dose may be expressed in absolute terms, for example in mg or μg of API deposited in the lungs. The deposited lung dose may also be expressed in relative terms, for example calculating the amount of API deposited as a percentage of the nominal dose.

"$C_{max}$" as used herein refers to the maximum plasma concentration for an active pharmaceutical ingredient (API).

"$C_{max}^{HEN}$" as used herein refers to the maximum blood plasma concentration for a nominal dose of the active pharmaceutical ingredient (API) administered with a high efficiency nebulizer.

"$C_{max}^{Conv}$" as used herein refers to the maximum blood plasma concentration for a nominal dose of the active pharmaceutical ingredient (API) administered with a conventional inhalation device.

$C_{max}$ can be determined by methods known to those of skill in the art. For example, the $C_{max}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by LC-MS/MS, plotting the concentration of API in each sample versus the time of collection after administration, and identifying the peak concentration of the API on the curve.

"Enhanced pharmacokinetic profile" means an improvement in some pharmacokinetic parameter. Pharmacokinetic parameters that may be improved include AUC (0-4 or 0-6 or 0-8 h), $AUC_{last}$, $AUC_{(0-\infty)}$, $T_{max}$, $T_{1/2}$, and $C_{max}$. In some embodiments, the enhanced pharmacokinetic profile may be measured quantitatively by comparing a pharmacokinetic parameter obtained for a nominal dose of an active pharmaceutical ingredient (API) administered by one route of administration, such as an inhalation device (e.g., a high efficiency nebulizer) with the same pharmacokinetic parameter obtained with the same nominal dose of active pharmaceutical ingredient (API) administered by a different route of administration, such as a different type of inhalation device or an oral formulation (e.g., oral tablet, oral capsule, or oral solution).

"Blood plasma concentration" refers to the concentration of an active pharmaceutical ingredient (API) in the plasma component of blood of a subject or patient population.

"Patient" or "subject" refers to the animal (especially mammal) or human being treated.

A "subject group" or "patient group" has a sufficient number of subjects or patients to provide a statistically significant average measurement of the relevant pharmacokinetic parameter. All members of the "subject group" or "patient group" have pharmacokinetic parameters for the mast cell stabilizers that fall within statistically normal ranges (i.e., there are no outliers), and no member is included on the basis of non-standard or unusual measurements.

"Nebulizer," as used herein, refers to a device that turns medications, compositions, formulations, suspensions, and mixtures, etc. into a fine aerosol mist for delivery to the lungs.

"Drug absorption" or simply "absorption" typically refers to the process of movement of drug from site of delivery of a drug across a barrier into a blood vessel or the site of action, e.g., a drug being absorbed via the pulmonary capillary beds of the alveoli into the systemic circulation.

"$T_{max}$" as used herein refers to the amount of time necessary for an active pharmaceutical ingredient (API) to attain maximum blood plasma concentration.

"$T_{max}^{HEN}$" as used herein refers to the amount of time necessary for a nominal dose of an active pharmaceutical ingredient (API) to attain maximum blood plasma concentration after administration with a high efficiency nebulizer.

"$T_{max}^{Conv}$" as used herein refers to the amount of time necessary for a nominal dose of an active pharmaceutical ingredient (API) to attain maximum blood plasma concentration after administration with a conventional inhalation device.

The term "treat" and its grammatical variants (e.g., "to treat," "treating," and "treatment") refer to administration of an active pharmaceutical ingredient to a patient with the purpose of ameliorating or reducing the incidence of one or more symptoms of a condition or disease state in the patient. Such symptoms may be chronic or acute; and such amelioration may be partial or complete. In the present context, treatment entails administering a mast cell stabilizer to a patient via any route of administration disclosed herein.

As used herein, the term "high concentration" refers to a concentration greater than 1% by weight. For example, in a specific embodiment, a "high concentration" formulation of cromolyn sodium comprises cromolyn sodium at a concentration of greater than 1% by weight.

As used herein, the term "hypotonic" refers to a formulation that has a tonicity less than 295 mOsm/kg.

The term "prophylaxis" refers to administration of an active pharmaceutical ingredient to a patient with the purpose of reducing the occurrence or recurrence of one or more acute symptoms associated with a disease state or a condition in the patient. In the present context, prophylaxis entails administering a mast cell stabilizer to a patient via any route of administration disclosed herein. Thus, prophylaxis includes reduction in the occurrence or recurrence rate of a systemic mast cell related disorder. However, prophylaxis is not intended to include complete prevention of onset of a disease state or a condition in a patient who has not previously been identified as suffering from the disease or the condition.

As used herein, a "systemically effective amount" is an amount of mast cell stabilizer in the body of a patient as a whole that is effective for the treatment or prophylaxis of a systemic mast cell related disorder. A "systemically effective amount" may be expressed, for example, as the mass of a mast cell stabilizer, or concentration of a mast cell stabilizer, in a patient's plasma. A "systemically effective amount" may differ depending on the specific mast cell stabilizer and the specific systemic mast cell related disorder.

As used herein, a difference is "significant" if a person skilled in the art would recognize that the difference is probably real. In some embodiments, significance may be determined statistically, in which case two measured parameters may be referred to as statistically significant. In some embodiments, statistical significance may be quantified in terms of a stated confidence interval (CI), e.g., greater than 90%, greater than 95%, greater than 98%, etc. In some embodiments, statistical significance may be quantified in terms of a p value, e.g., less than 0.5, less than 0.1, less than 0.05, etc. The person skilled in the art will recognize these expressions of significance and will know how to apply them appropriately to the specific parameters that are being compared.

Methods of Treating Systemic Mast Cell Related Disorders with Mast Cell Stabilizers Disclosed herein are methods for the treatment or prophylaxis of systemic mast cell related disorders comprising administering compositions comprising one or more mast cell stabilizers. As used herein, a "systemic mast cell related disorder" is a disease or condition that is caused by or associated with excessive proliferation or activation of mast cells or abnormal release of vasoactive or pro-inflammatory mediators in the body as a whole, and is thus treatable by administration of a systemically effective amount of a mast cell stabilizer, e.g., cromolyn sodium. A systemic mast cell related disorder is distinct from a local mast cell related disorder, in which symptoms of the disease or condition manifest in a particular region of the body. Systemic mast cell related disorders include, but are not limited to, a mast cell activation syndrome; mastocytosis; idiopathic urticaria; chronic urticaria; atopic dermatitis; idiopathic anaphylaxis; Ig-E and non Ig-E mediated anaphylaxis; angioedema; allergic disorders; irritable bowel syndrome; mastocytic gastroenteritis; mastocytic colitis; fibromyalgia; kidney fibrosis; atherosclerosis; myocardial ischemia; hypertension; congestive heart failure; pruritus; chronic pruritus; pruritus secondary to chronic kidney failure; heart, vascular, intestinal, brain, kidney, liver, pancreas, muscle, bone and skin conditions associated with mast cells; CNS diseases such as Parkinson's disease and Alzheimer's disease; metabolic diseases such as diabetes; sickle cell disease; autism; chronic fatigue syndrome; lupus; chronic lyme disease; interstitial cystitis; multiple sclerosis; cancer; migraine headaches; psoriasis; eosinophilic esophagitis; eosinophilic gastroenteritis; Churg-Strauss syndrome; hypereosinophilic syndrome; eosinophilic fasciitis; eosinophilic gastrointestinal disorders; chronic idiopathic urticaria; myocarditis; Hirschsprung's-associated enterocolitis; postoperative ileus; wound healing; stroke; transient ischemic attack; pain; neuralgia; peripheral neuropathy; acute coronary syndromes; pancreatitis; cutaneous mastocytosis; systemic mastocytosis; systemic indolent mastocytosis; dermatomyositis; fibrotic skin diseases; pain associated with cancer; ulcerative colitis; inflammatory bowel disease; radiation colitis; celiac disease; gluten enteropathy; radiation cystitis; painful bladder syndrome; hepatitis; hepatic fibrosis; cirrhosis; rheumatoid arthritis; lupus erythematosus; and vasculitis.

In some embodiments of the methods disclosed herein wherein the systemic mast cell related disorder is a CNS disease such as Parkinson's disease and Alzheimer's disease, a mast cell stabilizer is neuroprotective. In some embodiments of the methods disclosed herein wherein the systemic mast cell related disorder is a CNS disease such as Parkinson's disease and Alzheimer's disease, a mast cell stabilizer crosses the blood brain barrier. In some embodiments of the methods disclosed herein wherein the systemic mast cell related disorder is Alzheimer's disease, a mast cell stabilizer prevents amyloid-beta protein polymerization and/or plaque formation. In some embodiments of the methods disclosed herein wherein the systemic mast cell related disorder is a heart condition, a mast cell stabilizer is cardioprotective.

In some embodiments of the methods disclosed herein, a composition comprising a mast cell stabilizer is administered for the treatment or prophylaxis of a condition that is associated with a systemic mast cell related disorder, including but not limited to autoimmune disorders, inflammatory conditions, allergic diseases and conditions, and viral and bacterial infections.

In some embodiments of the methods disclosed herein, the number of mast cells in a patient is stabilized after administration of a composition comprising a mast cell stabilizer to the patient. In some embodiments of the methods disclosed herein, the activity of mast cells is stabilized in a patient after administration of a composition comprising a mast cell stabilizer to the patient. In some embodiments of the methods disclosed herein, one or more of total tryptase and histamine in a patient's blood, and prostaglandin D2, 11beta-prostaglandin F2-alpha, and N-methylhistamine in the patient's urine, is reduced after administration of a composition comprising a mast cell stabilizer to a patient.

As used herein, a "mast cell stabilizer" refers to an agent that inhibits degranulation and/or the release of pro-inflammatory and vasoactive mediators from mast cells. Mast cell stabilizers include, but are not limited to, cromolyn, dihydropyridines such as nicardipine and nifedipine, lodoxamide, nedocromil, barnidipine, YC-114, elgodipine, niguldipine, ketotifen, methylxanthines, quercetin, and pharmaceutically salts thereof. In some embodiments, the mast cell stabilizer is a pharmaceutically acceptable salt of cromolyn, such as cromolyn sodium, cromolyn lysinate, ammonium cromonglycate, and magnesium cromoglycate. In some embodiments, mast cell stabilizers include but are not limited to compounds disclosed in U.S. Pat. Nos. 6,207,684; 4,634,699; 6,207,684; 4,871,865; 4,923,892; 6,225,327; 7,060,827; 8,470,805; 5,618,842; 5,552,436; 5,576,346; 8,252,807; 8,088,935; 8,617,517; 4,268,519; 4,189,571; 3,790,580; 3,720,690; 3,777,033; 4,067,992; 4,152,448; 3,419,578; 4,847,286; 3,683,320; and 4,362,742; U.S. Patent Application Publication Nos. 2011/112183 and 2014/140927; European Patent Nos. 2391618; 0163683; 0413583; and 0304802; International Patent Application Nos. WO2010/042504; WO85/02541; WO2014/115098; WO2005/063732; WO2009/131695; and WO2010/088455; all of which are incorporated by reference. Mast cell stabilizers, including cromolyn and pharmaceutically acceptable salts, prodrugs, and adducts thereof, may be prepared by methods known in the art.

In some embodiments, mast cell stabilizers described herein may be prepared as prodrugs. A "prodrug" refers to an agent that is converted into the parent drug in vivo. The prodrug can be designed to alter the metabolic stability or the transport characteristics of a drug, to mask side effects or toxicity, to improve the flavor of a drug, or to alter other characteristics or properties of a drug. In some embodiments, the prodrug has improved bioavailability relative to the parent drug. In some embodiments, the prodrug has improved solubility in pharmaceutical compositions over the parent drug. In some embodiments, prodrugs may be designed as reversible drug derivatives, for use as modifiers to enhance drug transport to site-specific tissues. In some embodiments, a prodrug of a mast cell stabilizer is an ester of the mast cell stabilizer, which is hydrolyzed to the carboxylic acid, the parent mast cell stabilizer. In some embodiments, a prodrug comprises a short peptide (polyaminoacid) bonded to an acid group, wherein the peptide is metabolized in vivo to reveal the parent drug. In certain embodiments, upon in vivo administration, a prodrug is chemically converted to the biologically, pharmaceutically or therapeutically active form of the mast cell stabilizer. In certain embodiments, a prodrug is enzymatically metabolized by one or more steps or processes to the parent mast cell stabilizer. In certain embodiments, the mast cell stabilizer is a prodrug of cromolyn. In a specific embodiment, the prodrug of cromolyn is cromoglicate lisetil.

To produce a prodrug, a pharmaceutically active mast cell stabilizer compound is modified such that the active compound will be regenerated upon in vivo administration. In some embodiments, prodrugs of mast cell stabilizers are designed by virtue of knowledge of pharmacodynamic processes and drug metabolism in vivo. See, e.g., Nogrady (1985) *Medicinal Chemistry A Biochemical Approach*, Oxford University Press, New York, pages 388-392; Silverman (1992), *The Organic Chemistry of Drug Design and Drug Action*, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006.

In some embodiments, mast cell stabilizers described herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically labeled compounds described herein, for example those with isotopes such as deuterium, i.e., $^{2}H$, can afford certain therapeutic advantages resulting from greater metabolic stability, such as, for example, increased in vivo half-life or reduced dosage requirements. In certain embodiments, the mast cell stabilizer is isotopically labeled cromolyn, or a pharmaceutically acceptable salt thereof, such as cromolyn sodium. In some embodiments, the mast cell stabilizer is deuterium-labeled cromolyn sodium.

In some embodiments, mast cell stabilizers described herein may be PEGylated, wherein one or more polyethylene glycol (PEG) polymers are covalently attached to the mast cell stabilizers. In some embodiments, pegylated mast cell stabilizers increase the half-life of the mast cell stabilizers in the body. In some embodiments, pegylation of the mast cell stabilizers increases the hydrodynamic size of the mast cell stabilizers and reduces their renal clearance. In some embodiments, pegylation of the mast cell stabilizers increases the solubility of the mast cell stabilizers. In some embodiments, pegylation of the mast cell stabilizers protects the mast cell stabilizers from proteolytic degradation.

Mast cell stabilizers may be administered in the methods disclosed herein in a suitable dose or nominal dose as determined by one of ordinary skill in the art. In some embodiments, the mast cell stabilizer is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, about 30 mg/dose to about 50 mg/dose, or greater than about 100 mg/dose. In some embodiments, the mast cell stabilizer is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, cromolyn sodium is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, or about 30 mg/dose to about 50 mg/dose, or greater than about 100 mg/dose. In other embodiments, cromolyn sodium is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, further active agents other than a mast cell stabilizer that are effective for the treatment or prophylaxis of a systemic mast cell related disorder are administered or co-administered with the mast cell stabilizer. Such further active agents may be administered separately, or may be incorporated into a composition comprising a mast cell stabilizer. Such further active agents include, but are not limited to, leukotriene antagonists, steroidal and non-steroidal anti-inflammatory drugs, anti-allergies, β-agonists, anticolinergics, corticosteroids, testosterone derivatives, phosphodiesterase inhibitors, endothelin antagonists, mucolytics, antibiotics, antifungals, antivirals, antioxidants, vitamins, heparinoids, α-antitrypsin, lung surfactants, anti-inflammatory compounds, glucocorticoids, anti-infective agents, antibiotics, antifungals, antivirals, antiseptics, vasoconstrictors, vasodilators, wound healing agents, local anesthetics, peptides, and proteins.

Anti-inflammatory compounds which may be administered or co-administered with a mast cell stabilizer in the methods disclosed herein include but are not limited to betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, elastane-, prostaglandin-, leukotriene, bradykinin-antagonists, non-steroidal anti-inflammatory drugs (NSAIDs), such as ibuprofen and indometacin.

Anti-allergic agents which may be administered or co-administered with a mast cell stabilizer in the methods disclosed herein include but are not limited to glucocorticoids, nedocromil, cetirizine, loratidine, montelukast, roflumilast, ziluton, omalizumab, heparins and heparinoids and other antihistamines, azelastine, cetirizine, desloratadine, ebastine, fexofenadine, levocetirizine, loratadine.

Anti-infective agents which may be administered or co-administered with a mast cell stabilizer in the methods disclosed herein include but are not limited to benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cefuroxime, cefamandole, cefotiam), cefoxitins (cefoxitin, cefotetan, latamoxef, flomoxef), cefotaximes (cefotaxime, ceftriaxone, ceflizoxime, cefinenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; glycopeptides, including vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, tinidazole, bifonazole, ravuconazole, posaconazole, voriconazole, and ornidazole and other antifungals including flucytosin, griseofluvin, tonoftal, naftifine, terbinafine, amorolfine, ciclopiroxolamin, echinocandins, such as micafungin, caspofungin, anidulafungin; nitrofurans, including nitrofurantoin and nitrofuranzone; polyenes, including amphotericin B, natamycin, nystatin, flucocytosine; other antibiotics, including tithromycin, lincomycin, clindamycin, oxazolidinones (linezolids), ranbezolid, streptogramine A+B, pristinamycin A+B, virginiamycin A+B, dalfopristin/quinupristin (Synercid), chloramphenicol, ethambutol, pyrazinamide, terizidon, dapson, prothionamide, fosfomycin, fucidinic acid, rifampicine, isoniazid, cycloserine, terizidone, ansamycin, lysostaphin, iclaprim, mirocin B17, clerocidin, filgrastim, and pentamidine; antivirals, including aciclovir, ganciclovir, birivudine, valaciclovir, zidovudine, didanosine, thiacytidin, stavudine, lamivudine, zalcitabine, ribavirin, nevirapirine, delaviridine, trifluridine, ritonavir, saquinavir, indinavir, foscarnet, amantadine, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, tee tree oil, alpha-hederin, bisabolol, lycopodin, vitapherole; wound healing compounds including dexpantenol, allantoin, vitamins, hyaluronic acid, alpha-antitrypsin, inorganic and organic zinc salts/compounds, interferones (alpha, beta, gamma), tumor necrosis factors, cytokines, interleukins.

Mucolytics which may be administered or co-administered with a mast cell stabilizer in the methods disclosed herein include but are not limited to DNasc, P2Y2-agonists (denufosol), heparinoids, guaifenesin, acetylcysteine, carbocysteine, ambroxol, bromhexine, lecithins, myrtol, and recombinant surfactant proteins.

Local anesthetic agents which may be administered or co-administered with a mast cell stabilizer in the methods disclosed herein include but are not limited to benzocaine, tetracaine, procaine, lidocaine and bupivacaine.

Peptides and proteins which may be administered or co-administered with a mast cell stabilizer in the methods disclosed herein include but are not limited to antibodies against toxins produced by microorganisms, antimicrobial peptides such as cecropins, defensins, thionins, and cathelicidins.

Immunomodulators which may be administered or co-administered with a mast cell stabilizer in the methods disclosed herein include but are not limited to methotrexate, azathioprine, cyclosporine A, tacrolimus, sirolimus, rapamycin, mycophenolate, mofetil, cytostatics and metastasis inhibitors, alkylants, such as nimustine, melphanlane, carmustine, lomustine, cyclophosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinum, cisplatinum and metallocene compounds such as titanocendichloride; amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab.

Proteinase inhibitors which may be administered or co-administered with a mast cell stabilizer in the methods disclosed herein include but are not limited to alpha-antitrypsin; antioxidants, such as tocopherols, glutathion; pituitary hormones, hypothalamic hormones, regulatory peptides and their inhibiting agents, corticotropine, tetracosactide, choriogonandotropine, urofolitropine, urogonadotropine, somatotropine, metergoline, desmopressine, oxytocine, argipressin, ornipressine, leuproreline, triptoreline, gonadoreline, busereline, nafareline, goselerine, somatostatine; parathyroid gland hormones, calcium metabolism regulators, dihydrotachysterole, calcitonine, clodronic acid, etidronic acid; thyroid gland therapeutics; sex hormones and their inhibiting agents, anabolics, androgens, estrogens, gestagenes, antiestrogenes; anti-migraine drugs, such as proxibarbal, lisuride, methysergide, dihydroergotamine, ergotamine, clonidine, pizotifene; hypnotics, sedatives, benzodiazepines, barbiturates, cyclopyrrolones, imidazopyridines, antiepileptics, zolpidem, barbiturates, phenyloin, primidone, mesuximide, ethosuximide, sultiam, carbamazepin, valproic acid, vigabatrine; antiparkinson drugs, such as levodopa, carbidopa, benserazide, selegiline, bromocriptine, amantadine, tiapride; antiemetics, such as thiethylperazine, bromopride, domperidone, granisetrone, ondasetrone, tropisetrone, pyridoxine; analgesics, such as buprenorphine, fentanyl, morphine, codeine, hydromorphone, methadone; fenpipramide, fentanyl, piritramide, pentazocine, buprenorphine, nalbuphine, tilidine; drugs for narcosis, such as N-methylated barbiturates, thiobarbiturates, ketamine, etomidate, propofol, benzodiazepines, droperidol, haloperidol, alfentanyl, sulfentanyl; antirheumatism drugs including tumor necrosis factor-alfa, nonsteroidal antiinflammatory drugs; antidiabetic drugs, such as insulin, sulfonylurea derivatives, biguanids, glitizols, glucagon, diazoxid; cytokines, such as interleukines, interferones, tumor necrosis factor (TNF), colony stimulating factors (GM-CSF, G-CSF, M-CSF); proteins, e.g. epoctine, and peptides, e.g. parathyrin, somatomedin C; heparine, heparinoids, urokinases, streptokinases, ATP-ase, prostacycline, sexual stimulants, and genetic material.

Formulations for the Administration of Mast Cell Stabilizers

In some embodiments, formulations administered in the methods disclosed herein produce in a human subject group an average $AUC_{(0-\infty)}$ of a mast cell stabilizer greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments, formulations administered in the methods disclosed herein produce in a human subject group an average $AUC_{(0-\infty)}$ of a mast cell stabilizer of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments, formulations administered in the methods disclosed herein produce in a human subject group an average $AUC_{(0-\infty)}$ of cromolyn sodium greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments, formulations administered in the methods disclosed herein produce in a human subject group an average $AUC_{(0-\infty)}$ of cromolyn sodium of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments, formulations administered in the methods disclosed herein produce in a human subject group an average $C_{max}$ of a mast cell stabilizer greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments, formulations administered in the methods disclosed herein produce in a human subject group an average $C_{max}$ of a mast cell stabilizer of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

In some embodiments, formulations administered in the methods disclosed herein produce in a human subject group an average $C_{max}$ of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments, formulations administered in the methods disclosed herein produce in a human subject group an average $C_{max}$ of cromolyn sodium of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

Mast cell stabilizers may be administered to a subject in the methods disclosed herein by multiple administration routes, either alone or concurrently, including but not limited to oral, oral inhalation, parenteral (e.g., intravenous, subcutaneous, intramuscular), implants such as osmotic pumps and depot implants, intranasal, buccal, topical, rectal, transdermal, vaginal, or sublingual administration routes. In some embodiments of the methods disclosed herein, mast cell stabilizers may be administered by a single route of administration. For example, in certain specific embodiments, the methods disclosed herein comprise administration of a mast cell stabilizer, such as cromolyn sodium, with an inhalation device, e.g., a high efficiency nebulizer, without coadministration of a mast cell stabilizer, e.g., cromolyn sodium, by another route of administration, e.g., an oral solution.

Mast cell stabilizers may be formulated into any suitable dosage form, including but not limited to aerosols, aqueous oral dispersions, solid oral dosage forms, self-emulsifying dispersions, solid solutions, liposomal dispersions, pegylated liposomes, liquids, gels, implants, depots, syrups, elixirs, slurries, suspensions, lotions, gels, pastes, medicated sticks, balms, creams, ointments, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, mixed immediate release formulations, controlled release formulations, enemas, rectal gels, rectal foams, rectal aerosols, vaginal gels, vaginal foams, vaginal aerosols, suppositories, jelly suppositories, or retention enemas. Such formulations may be manufactured in a conventional manner, such as, by way of example only, conventional mixing, dissolving, granulating, dragee-making, levigating, emulsifying, encapsulating, entrapping or compression processes.

In some embodiments, the formulations disclosed herein may include one or more inactive ingredients or pharmaceutical excipients that provide suitable properties of the formulation. Such inactive ingredients may include one or more of the following classes.

"Albumin" refers to a family of globular proteins, the most common of which is serum albumin. Albumins are commonly found in blood plasma and function to regulate colloidal osmotic pressure of the blood. Albumin proteins found in the plasma bind some pharmaceutical compounds to form complexes. Complexation of albumin with pharmaceutical compounds, e.g., mast cell stabilizers, can influence the pharmaceutical compounds' plasma half-life and/or biological half-life in the body by preventing metabolism and/or excretion of the complexed compounds. In some embodiments, compositions disclosed herein include albumin and a mast cell stabilizer, e.g., cromolyn sodium.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Carriers" or "carrier materials" include any commonly used excipients in pharmaceutics and should be selected on the basis of compatibility with the specific mast cell stabilizer and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents" and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween 60 or 80, PEG, Tyloxapol, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

"Diluent" refers to chemical compounds that are used to dilute the compound of interest prior to delivery. Diluents can also be used to stabilize compounds because they can provide a more stable environment. Salts dissolved in buffered solutions, including, but not limited to, a phosphate buffered saline solution, are utilized as diluents in the art, and can also provide pH control or maintenance. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents" or "disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids. Combinations of one or more erosion facilitator with one or more diffusion facilitator can also be used in the present compositions.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dentomint, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

In certain embodiments, compositions provided herein may also include one or more preservatives to inhibit microbial activity. Suitable preservatives include mercury-containing substances such as merfen and thiomersal; stabilized chlorine dioxide; octinidine; and quaternary ammonium compounds such as benzalkonium chloride, cetyltrimethylammonium bromide and cetylpyridinium chloride.

"Solubilizers" include compounds such as triacetin, triethylcitrate, ethyl oleate, ethyl caprylate, sodium lauryl sulfate, sodium doccusate, vitamin E TPGS, polysorbates (Tweens) dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, e.g., citric acid, EDTA and pharmaceutically acceptable salts thereof, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

It should be appreciated that there is considerable overlap between classes of inactive ingredients. Thus, the above-listed ingredients should be taken as merely exemplary, and not limiting, of the types of inactive ingredients that can be included in formulations described herein. The amounts of such inactive ingredients can be readily determined by one skilled in the art, according to the particular properties desired.

In certain specific embodiments, formulations for administration of mast cell stabilizers in the methods disclosed herein include, but are not limited to, Aararre, Acecromol, Acromax, Acticrom, Aeropaxyn, Alercom, Alercrom, Alercrom Nasal, Alerg, Alerg AT, Alerg Nasenspray, Alergocrom, Alerion, Allercrom, Allerg-Abak, Allergo-COMOD, Allergocomod, Allergocrom, Allergocrom Kombi, Allergocrom Kombinationspackung, Allergojovis, Allergostop, Allergotin, Allergoval, Allersol, Alloptrex, Apo-Cromolyn, Botastin, Brol-Eze, Chromosol Ophta, Clariteyes, Clarityn Allergy Eyedrops, Clarityn Eye Drops, Claroftal, Clo-5, Coldacrom, Colimune, Croglina, Crolidin, Crolom, Crom-Ophtal, Crom-Ophtal Kombipackung, Crom-Ophtal Sine, Cromabak, Cromadoses, Cromal, Cromantal, Cromedil, Cromedil Unidose, Cromese, Cromex, Cromo, Cromo Asma, Cromo EDP, Cromo Einzeldosis, Cromo Kombipackung, Cromo UD, Cromo-Comod, Cromo-Pos, Cromo-Spray, Cromobene, Cromocato, Cromodyn, Cromoftal, Cromogen, Cromoglicin, Cromohexal, Cromohexal Kombipackung, Cromohexal UD, Cromol, Cromolerg, Cromolergin UD, Cromolind, Cromolux, Cromophtal, Cromopp, Cromoptic, Cromoptic Unidose, Cromorhinol, Cromosan, Cromosoft, Cromosol, Cromosol UD, Cromovet, Cromunal, Cronacol, Cronase, Cropoz, Cropoz G, Cropoz N, Crorin, Cusicrom, Cusilyn, Diffusyl, Dilospir, Dispacromil, Dispacromil Sine, DNCG, DNCG PPS, Duobetic, Duracroman, Erystamine-K, Esirhinol, Exaler, Farmacrom, Fenistil Eye Drops, Fenolip, Fintal, Fivent, Flenid, Flui-DNCG, Fluvet, Frenal, Gaster, Gastrocrom, Gastrofrenal, Gelodrin, Gen-Cromoglycate, Gen-Cromoglycate Sterinebs, Gen-Cromolyn, Glicacil, Glicinal, Glinor, Hay-Crom, Hayfever Eye Drops, Hexacroman, Humex Conjonctivite Allergique, Ifiral, Indoprex, Inostral, Intal, Intal 5, Intal Forte, Intal N, Intal Nasal, Intal Nebulizador, Intal Nebulizer, Intal Spincaps, Intal Syncroner, Intercron, Introl, Iopanchol, Kaosyl, Kiddicrom, Klonalcrom, Lecrolyn, Logomed Heuschnupfen-Spray, Lomudal, Lomudal Nebuliser, Lomudal sans FCKW, Lomudas, Lomupren, Lomusol, Lomuspray, Maxicrom, Multicrom, Multicrom Unidose, Nalcrom, Nalcron, Nasalcrom, Nasivin gegen Heuschnupfen, Nasmil, Natriumcromoglicaat, Nebulasma, Nebulcrom, Novacro Novo-Cromolyn, Novo-Cromolyn Nebulizer, Nu-Cromolyn Plast Ophtacalm, Ophtacalm Unidose, Opticrom, Opticrom Allergy, Opticrom Aqueous, Opticrom UD, Opticron, Opticron Unidose, Optrex Hayfever Allergy, Oralcrom, Otriven H, Otrivin Hooikoorts, Padiacrom, Pentacrom, Pentatop, PMS-Sodium Cromoglycate, Poledin, Pollenase Allergy, Pollyferm, Prevalin, Primover, Prothanon Cromo, Pulbil, Pulmosin, Renocil, Resiston Two, Rhinaris-CS Anti-Allergic Nasal Mist, Rilan, Rinil, Rinilyn, Rinofrenal, Rynacrom, Rynacrom M, Sificrom, Sofro, Solu-Crom, Spaziron, Spralyn, Stadaglicin, Steri-Neb Cromogen, Stop-Allerg, Taleum, Ufocollyre, Vekfanol, Vicrom, Vistacrom, Vivicrom, Vividrin, Vividrin iso EDO, Viz-On, Zineli, or Zulboral.

Solid Oral Formulations

In some embodiments, the solid dosage forms disclosed herein may be in the form of a tablet, (including a suspension tablet, a fast-melt tablet, a bite-disintegration tablet, a rapid-disintegration tablet, an effervescent tablet, an osmotic pump tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, or granules. In some embodiments, systemically effective amounts of mast cell stabilizers are achieved with solid oral formulations by including one or more of permeation enhancers and enteric coatings in the solid oral formulations. In some embodiments, enteric coatings regulate the delivery a mast cell stabilizer during its passage through the stomach and intestine.

The pharmaceutical solid dosage forms described herein can include a mast cell stabilizer and one or more pharmaceutically inactive ingredients such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In some embodiments, solid dosage forms, e.g., tablets, effervescent tablets, and capsules, are prepared by mixing particles of a mast cell stabilizer with one or more pharmaceutical excipients to form a bulk blend composition. When referring to these bulk blend compositions as homogeneous, it is meant that the particles of the mast cell stabilizer are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques, e.g., one or a combination of: (1) dry mixing, (2) direct compression, (3) milling, (4) dry or non-aqueous granulation, (5) wet granulation, and (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Pharmaceutical preparations for oral use can be obtained by mixing one or more solid excipient with one or more mast cell stabilizers, optionally grinding the resulting mixture, and processing the mixture of granules, after adding suitable auxiliaries, if desired, to obtain tablets or dragee cores. In some embodiments, dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In other embodiments, a powder including a mast cell stabilizer may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

Compressed tablets are solid dosage forms prepared by compacting the bulk blend of the formulations described above. In some embodiments, the compressed tablets will include a film surrounding the final compressed tablet. In some embodiments, the film coating can provide a delayed release of the mast cell stabilizer from the formulation. In other embodiments, the film coating aids in patient compliance. Film coatings such as Opadry® typically range from about 1% to about 3% of the tablet weight. In other embodiments, the compressed tablets include one or more pharmaceutical excipients.

A capsule may be prepared, for example, by placing the bulk blend of the formulation of the mast cell stabilizer inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In some embodiments, dosage forms may include microencapsulated formulations. Materials useful for the microencapsulation include materials compatible with mast cell stabilizers, which sufficiently isolate mast cell stabilizers from other non-compatible excipients. Materials compatible with mast cell stabilizers are those that delay the release of the mast cell stabilizers in vivo. Exemplary microencapsulation materials useful for delaying the release of the formulations include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials. In some embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material.

Microencapsulated mast cell stabilizers may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In other embodiments, the formulations described herein are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the mast cell stabilizer and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

In other embodiments, formulations described herein include a matrix based dosage form. In a matrix-based dosage form described herein, at least one mast cell stabilizer and optional pharmaceutically acceptable excipient(s) are dispersed within a polymeric matrix, which typically comprises one or more water-soluble polymers and/or one or more water-insoluble polymers. The drug can be released from the dosage form by diffusion and/or erosion. Suitable water-soluble polymers include, but are not limited to, polyvinyl alcohol, polyvinylpyrrolidone, methylcellulose, hydroxypropylcellulose, hydroxypropylmethylcellulose, or polyethylene glycol, and/or mixtures thereof. Suitable water-insoluble polymers also include, but are not limited to, ethylcellulose, cellulose acetate, cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride) or polyurethane, and/or mixtures thereof. Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, EXPLOTAB, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients can have more than one role or function, or can be classified in more than one group; the classifications are descriptive only, and are not intended to limit any use of a particular excipient.

Matrix formulations of the present invention can be prepared by using, for example, direct compression or wet granulation. A functional coating can then be applied. Additionally, a barrier or sealant coat can be applied over a matrix tablet core prior to application of a functional coating. The barrier or sealant coat can serve the purpose of separating an active ingredient from a functional coating, which can interact with the active ingredient, or it can prevent moisture from contacting the active ingredient.

In some embodiments, the modified-release formulations described herein are provided as osmotic pump dosage forms. In an osmotic pump dosage form, a core containing at least one mast cell stabilizer and optionally at least one osmotic excipient is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form can contain two internal compartments in the core. The first compartment contains the drug and the second compartment can contain a polymer, which swells on contact with aqueous fluid. After ingestion, this polymer swells into the drug-containing compartment, diminishing the volume occupied by the drug, thereby forcing the drug from the device at a controlled rate over an extended period of time. Such dosage forms are often used when a zero order release profile is desired. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as to increase the hydrostatic pressure within the dosage form. The polymers can swell or expand to a very high degree, usually exhibiting a 2- to 50-fold volume increase. The polymers can be non-cross-linked or cross-linked. In some embodiments, the swellable polymers are hydrophilic polymers.

In some embodiments, mast cell stabilizers can be provided in a multiparticulate membrane-modified formulation. Membrane-modified formulations can be made by preparing a rapid release core, which can be a monolithic (e.g., tablet) or multi-unit (e.g., pellet) type, and coating the core with a membrane. The membrane-modified core can then be further coated with a functional coating. In between the membrane-modified core and functional coating, a barrier or sealant can be applied. The mast cell stabilizer can be formed into an active core by applying the compound to a nonpareil seed. The at least one mast cell stabilizer can be applied with or without additional excipients onto the inert cores, and can be sprayed from solution or suspension using a fluidized bed coater (e.g., Wurster coating) or pan coating system. Alternatively, a mast cell stabilizer can be applied as a powder onto the inert cores using a binder to bind the mast cell stabilizer onto the cores. Active cores can also be formed by extrusion of the core with suitable plasticizers and any other processing aids as necessary.

The pharmaceutical solid oral dosage forms described herein can be further formulated to provide a controlled release of the mast cell stabilizer. Controlled release refers to the release of the mast cell stabilizer from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to shellac acrylic polymers, cellulose derivatives, and poly vinyl acetate phthalate (PVAP).

Conventional coating techniques such as spray or pan coating are employed to apply coatings. The coating thickness must be sufficient to ensure that the oral dosage form remains intact until the desired site of topical delivery in the intestinal tract is reached.

Liquid Oral Formulations

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, 2$^{nd}$ Ed., pp. 754-757 (2002). In addition to the particles of a mast cell stabilizer, the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor. In some embodiments, systemically effective amounts of mast cell stabilizers are achieved with liquid oral formulations by including permeation enhancers in the liquid oral formulations.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Intranasal Formulations

Intranasal formulations are known in the art and are described in, for example, U.S. Pat. Nos. 4,476,116, 5,116,817 and 6,391,452, each of which is specifically incorporated by reference. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, viscosity enhancing agents, preservatives, surfactants, gelling agents, or buffering and other stabilizing and solubilizing agents may also be present. In some embodiments, the nasal dosage form is isotonic with nasal secretions. In some embodiments a nasal dosage form is formulated to achieve sustained delivery. Examples of sustained delivery nasal dosage forms include, but are not limited to, dosage forms that include mucoadhesive agents such as microcrystalline cellulose. In some embodiments, systemically effective amounts of mast cell stabilizers are achieved with intranasal formulations by one or more of optimizing the droplet or particle size and including permeation enhancers in the intranasal formulation.

Buccal Formulations

Buccal formulations that include mast cell stabilizers may be administered using a variety of formulations known in the art. For example, such formulations include, but are not limited to, those described in U.S. Pat. Nos. 4,229,447, 4,596,795, 4,755,386, and 5,739,136, each of which is specifically incorporated by reference. In addition, the buccal dosage forms can further include a bioerodible (hydrolysable) polymeric carrier that also serves to adhere the dosage form to the buccal mucosa. The buccal dosage form is fabricated so as to erode gradually over a predetermined time period, wherein the delivery of the mast cell stabilizer is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the mast cell stabilizer and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. In some embodiments, systemically effective amounts of mast cell stabilizers are achieved with buccal formulations by one or more of optimizing the erosion time of the formulation and by including permeation enhancers in the buccal formulations.

Transdermal Formulations

Transdermal formulations described herein may be administered using a variety of devices which have been described in the art. For example, such devices include, but are not limited to, those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

Transdermal dosage forms for use in the methods disclosed herein may incorporate certain pharmaceutically acceptable excipients which are conventional in the art. In one embodiment, the transdermal formulations include at least three components: (1) a formulation of a mast cell stabilizer; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin. In some embodiments, systemically effective amounts of mast cell stabilizers are achieved with transdermal dosage forms by including skin permeation enhancers in the transdermal dosage forms.

Transdermal formulations used in the methods described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of mast cell stabilizers can be accomplished by means of iontophoretic patches, microneedle systems, and the like. Additionally, transdermal patches can provide controlled delivery of the mast cell stabilizer. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In some embodiments, transdermal delivery of a mast cell stabilizer, e.g., cromolyn sodium, is provided using topical formulations of the mast cell stabilizer, e.g, cromolyn sodium.

Injectable Formulations

Formulations that include a mast cell stabilizer suitable for intramuscular, subcutaneous, or intravenous injection may contain physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Pharmaceutical formulations for parenteral administration include aqueous solutions of the mast cell stabilizers in water-soluble form. Additionally, suspensions of the mast cell stabilizers may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use. In some embodiments, parenteral formulations are prepared to provide sustained release of a mast cell stabilizer. In some embodiments, sustained release is provided by incorporating liposomes, stealth liposomes, bioerodible polymers, and the like into parenteral formulations to maximize the residence time in circulation and/or to increase absorption of the mast cell stabilizer.

Implantable Formulations

Formulations that include a mast cell stabilizer suitable for implantation may contain physiologically acceptable sterile aqueous or non-aqueous solutions, dispersions, suspensions, or emulsions. In some embodiments, the formulations are contained in and delivered from an osmotic pump implant to achieve sustained delivery of the mast cell stabilizer over long durations. In some embodiments, a mast cell stabilizer is formulated with a bioerodible polymer, which, upon administration facilitates the formation of a depot containing the mast cell stabilizer. The depot would then erode and release the mast cell stabilizer over a duration determined by the composition of the bioerodible polymer. In some embodiments, viscosity modifying agents, stabilizers, and other excipients may be used in the formulation to achieve optimum delivery over an extended duration.

Inhalation Therapy

An "inhalation device," as used herein, refers to any device that is capable of administering a drug formulation to the respiratory airways of a patient. Inhalation devices include conventional inhalation devices such as metered dose inhalers (MDIs), dry powder inhalers (DPIs), jet nebulizers, ultrasonic wave nebulizers, heat vaporizers, and soft mist inhalers. Inhalation devices also include high efficiency nebulizers. Nebulizers, metered dose inhalers, and soft mist inhalers deliver pharmaceuticals by forming an aerosol which includes droplet sizes that can easily be inhaled. The aerosol can be used by a patient within the bounds of an inhalation therapy, whereby the mast cell stabilizer reaches the patient's respiratory tract upon inhalation. In some embodiments, the methods disclosed herein comprise administering to a patient a nominal dose of a mast cell stabilizer by an inhalation device. In some embodiments of the methods disclosed herein, an inhalation device is not a bronchoscope.

In some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a systemic mast cell related disorder because both a systemically effective amount of the mast cell stabilizer and a high deposited lung dose of the mast cell stabilizer is achieved in the patient. Thus, in some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a systemic mast cell related disorder that is not believed to be susceptible to treatment or prophylaxis with a mast cell stabilizer because both a systemically effective amount of the mast cell stabilizer and a high deposited lung dose of the mast cell stabilizer are achieved in the patient. Furthermore, in some embodiments where a mast cell stabilizer is administered with an inhalation device, e.g., a high efficiency nebulizer, a dry powder inhaler, a metered dose inhaler, a thermal aerosol inhaler, or an electrohydrodynamic-based solution misting inhaler, the methods disclosed herein provide improved efficacy for the treatment or prophylaxis of a systemic mast cell related disorder relative to administration of a systemically effective amount of the mast cell stabilizer by a different route of administration, e.g., parenterally or orally, because administration of the mast cell stabilizer with an inhalation device, e.g., a high efficiency nebulizer, a dry powder inhaler, a metered dose inhaler, a thermal aerosol inhaler, or an electrohydrodynamic-based solution misting inhaler, provides both a systemically effective amount of the mast cell stabilizer and a high deposited lung dose of the mast cell stabilizer in the patient. In some embodiments, a systemically effective amount of a mast cell stabilizer is achieved by delivering the mast cell stabilizer in an aerosol generated by a vibrating mesh nebulizer that produces droplets with a MMD of 3.0-4.0 μm and a GSD of 1.5-1.8. In some embodiments of the methods disclosed herein, an aerosol is administered through a mouthpiece of a nebulizer using normal tidal breathing.

Characterization of Inhalation Devices

The efficiency of a particular inhalation device can be characterized in many different ways, including by pharmacokinetic properties, lung deposition (deposited lung dose), respirable dose (RD), delivered dose (DD), respirable fraction (RF), respirable drug delivery rate (RDDR), volumetric or mass median diameter (VMD or MMD), mass median aerodynamic diameter (MMAD) in combination with the geometric standard deviation (GSD), and total output rate (TOR), among others. The MMAD and GSD can be measured using a cascade impactor as described in United States Pharmacopoeia (USP<1601>). The DD can be measured by using breath simulation apparatus as described in USP<1601>. The RF is derived from measuring the amount of drug deposited on the cascade impactor plates with a particular cut-off particle size, and expressing that as a fraction of the total amount deposited on the cascade impactor plates, the induction port and the filter. The RD is calculated by multiplying the DD by the RF. The TOR is measured by the difference in weight of the nebulizer before and after completion of nebulization divided by the duration of nebulization. VMD or MMD can be measured with a standard laser light scattering apparatus such as the Malvern Spraytec.

Pharmacokinetics is concerned with the uptake, distribution, metabolism and excretion of a drug substance. A pharmacokinetic profile comprises one or more biological measurements designed to measure the absorption, distribution, metabolism and excretion of a drug substance. One way of visualizing a pharmacokinetic profile is by means of a blood plasma concentration curve, which is a graph depicting mean active ingredient blood plasma concentration on the Y-axis and time (usually in hours) on the X-axis. Some pharmacokinetic parameters that may be visualized by means of a blood plasma concentration curve include $AUC_{last}$, $AUC_{(0-\infty)}$, $C_{max}$, $T_{1/2}$, and $T_{max}$. An enhanced pharmacokinetic profile in a patient can be indicated by increased $AUC_{last}$, $AUC_{(0-\infty)}$, $C_{max}$, or $T_{1/2}$, a decreased $T_{max}$, or an increased $T_{max}$. Enhanced levels of a mast cell stabilizer in the blood plasma of a patient may result in better control of or improved symptoms of a systemic mast cell related disorder.

The deposited lung dose may be expressed as a percentage of the nominal dose that is deposited in the lung. For example, a lung deposition of 30% means 30% of the nominal dose is deposited in the lung. Likewise, a lung deposition of 60% means 60% of the nominal dose is deposited in the lung, and so forth. Lung deposition (deposited lung dose) can be determined using methods of scintigraphy or deconvolution.

RF, DD, RD, and RDDR are calculated parameters based on in vitro data that provide technical dimensions for the efficiency of an inhalation device. RF represents the percentage of the delivered aerosol, or inhaled mass, that penetrates into the gas-exchange region of the lungs. RF may be measured with a cascade impactor or laser diffraction apparatus. RF is expressed herein as the percentage of an aerosol delivered with an inhalation device that has a particular particle diameter or range of particle diameters. For example, the term "RF (≤3.3 μm)" as used herein refers to the percentage of an aerosol delivered with an inhalation device that has a particle diameter less than or equal to 3.3 μm. Similarly, the terms "RF (1-5 μm)" and "RF (≤5 μm)" as used herein refer to the percentage of an aerosol delivered with an inhalation device that has a particle diameter in the range of 1 μm to 5 μm, or less than 5 μm, respectively. DD is the portion or percentage of the nominal dose that is actually emitted from the mouthpiece of the device. The difference between the nominal dose and the DD is the amount of drug lost primarily as residues, i.e., the amount of drug remaining in the inhalation device after administration or lost in aerosol form. RD is an expression of the delivered mass of drug contained within droplets or particles having a certain diameter emitted from an inhalation device, such as a DPI, MDI, or nebulizer, that are small enough to penetrate into the lung of a patient. The RD is determined by multiplying the DD by the RF. RDDR is the speed at which a respirable dose of the drug is delivered to a patient's lungs. RDDR, measured as a function of μg or mg/min, is determined by dividing the RD by the amount of time necessary for inhalation. The amount of time necessary for inhalation is measured as the amount of time from the first moment of administration of the emitted droplet or powder from the nebulizer, DPI, or MDI until the emitted or delivered droplet or powder of a respirable diameter is delivered to the lung.

Aerosol particle/droplet size is one factor determining the deposition of aerosol drugs in the airways. The distribution of aerosol particle/droplet size can be expressed in terms of one or more of VMD/MMAD and GSD. GSD is a dimensionless measure of a droplet size distribution curve relevant for characterizing terms such as VMD, MMD, and MMAD. In general, the smaller the GSD for a particular particle size distribution, the narrower the distribution curve.

Conventional Inhalation Devices

Conventional inhalation devices may be mechanical or electrical, and include, for example, jet nebulizers and ultrasonic nebulizers. Jet nebulizers generally utilize compressors to generate compressed air, which breaks the liquid medication into small breathable droplets, which form an aerosolized (atomized) mist. In some embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap. Some nebulizers may provide the aerosol in a continuous mode (e.g., the eFlow from PARI Pharma Starnberg), by a breath enhanced mode (e.g., the PARI LC Plus or Sprint from PART Starnberg), by breath actuated mode dependent on the breathing pattern of the patient (e.g., the AeroEclipse from Trudell, Canada or the I-Neb from Philips Respironics), or according to given inhalation profile (e.g., the Akita from Activaero, Gmuenden, Germany).

Some conventional inhalation devices are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety. Commercial conventional inhalation devices are available from: PARI (Germany) under the trade names PART LC Plus®, LC Star®, and PART-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

In some embodiments of the methods disclosed herein, compositions comprising mast cell stabilizers are administered with a dry powder inhaler. In some embodiments of the methods disclosed herein, compositions administered with dry powder inhalers comprise one or more of nanoparticles, spray dried materials, engineered porous particles with low mass median diameter but a high geometric diameter, liposomes, and stealth (or PEGylated) liposomes. In some embodiments, compositions administered by dry powder inhalers administered in the methods disclosed herein comprise nanoparticle clusters that aggregate into micrometer sized particles at neutral or basic pH but dissociate into nanoparticles at the pH encountered in the lung. In some embodiments the nanoparticle clusters comprise fumaryl diketopiperazine. In some embodiments, compositions administered with dry powder inhalers comprise lactose. In some embodiments, compositions administered with dry powder inhalers do not comprise lactose. In some embodiments, compositions administered with a dry powder inhaler have a MMAD between 2 and 4 μm, a GSD between 1.5 and 2.5 μm, and an RF (≤5 μm) between 30% and 80%. In some embodiments, a dry powder inhaler used to administer an inhalation formulation in the methods disclosed herein comprises a pre-metered dose, such as Plastiape Monodose inhaler, which comprises a capsule pre-filled with a powder. In some embodiments, a dry powder inhaler used to administer an inhalation formulation in the methods disclosed herein has a device-metered system such as Twisthaler, sold by Schering Plough, which comprises a reservoir to store a powder and a twisting top to dispense each dose. Inhalation formulations for administration with a dry powder inhaler may be prepared by blending a mast cell stabilizer, e.g., cromolyn sodium, with lactose, or spray drying a mast cell stabilizer, e.g., cromolyn sodium, or by pelletizing a mast cell stabilizer, e.g., cromolyn sodium, to form free-flowing spherical agglomerates.

In some embodiments of the methods disclosed herein, compositions comprising mast cell stabilizers are administered with a metered dose inhaler. In some embodiments, a composition administered with a metered dose inhaler in the methods disclosed herein comprises one or more of nanoparticles, spray dried materials, engineered porous particles with low mass median diameter but a high geometric diameter, liposomes, and stealth (or PEGylated) liposomes.

In some embodiments of the methods disclosed herein, compositions comprising mast cell stabilizers are administered with a thermal aerosol inhaler. In some embodiments, the aerosol in a thermal aerosol inhaler is generated by directly heating and vaporizing a thin solid film of the mast cell stabilizer, e.g., cromolyn sodium, or by heating and vaporizing a solution of a mast cell stabilizer, e.g., cromolyn sodium in solvents such as propylene glycol and/or glycerol and water.

In some embodiments of the methods disclosed herein, compositions comprising mast cell stabilizers are administered with an electrohydrodynamic-based solution misting inhaler.

In some embodiments, the aerosol in the electrohydrodynamic-based solution-misting inhaler is generated by subjecting a solution of a mast cell stabilizer, e.g., cromolyn sodium, or a liposome or pegylated liposome comprising a mast cell stabilizer, e.g., cromolyn sodium, to electrohydrodynamic forces through electrostatic energy.

High Efficiency Nebulizers

High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. Still yet, in some embodiments, the high efficiency nebulizer contains a pulsating membrane. In some embodiments, the high efficiency nebulizer is continuously operating.

In some embodiments, the high efficiency nebulizer contains a vibrating micro-perforated membrane of tapered nozzles that generates a plume of droplets without the need for compressed gas. In these embodiments, a solution in the micro-perforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments of high efficiency nebulizers use passive nozzle membranes and a separate piezoelectric transducer that stimulates the membrane. In contrast, some high efficiency nebulizers employ an active nozzle membrane, which use the acoustic pressure in the nebulizer to generate very fine droplets of solution via the high frequency vibration of the nozzle membrane.

Some high efficiency nebulizers contain a resonant system. In some such high efficiency nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the high efficiency nebulizer may be made stainless steel, or of a nickel-palladium alloy by electroforming.

In some embodiments, a high efficiency nebulizer may be adapted or adaptable to operate in conjunction with a unit dosage form, such as an ampule or vial, which contains a single dose of a mast cell stabilizer composition for the treatment of a systemic mast cell related disorder. The unit dosage form comprises a container that contains an inhalation formulation comprising the mast cell stabilizer, such as cromolyn sodium. The container is adapted to cooperate with the high efficiency nebulizer device in such a way as to permit administration of the nominal dose of the inhalation formulation to a patient. In some embodiments, the high efficiency nebulizer and the unit dosage form are configured so that they are useable together, but not with other devices or dosage forms. In some particular embodiments, the unit dosage form is configured such that it fits into a keyhole-like structure in the high efficiency nebulizer, but will not operate with other nebulizer devices. In such embodiments, the high efficiency nebulizer is configured such that it will accept and properly operate with the unit dosage form containing the mast cell stabilizer, but not with other dosage forms.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®.

In some embodiments, the methods disclosed herein comprise administration to a patient a nominal dose of a mast cell stabilizer with a high efficiency nebulizer, wherein administration of the nominal dose of the mast cell stabilizer to the patient provides one or more of the following advantages: (1) an enhanced pharmacokinetic profile as compared to administration of an oral solution or an inhalation formulation with a conventional inhalation device; (2) an enhanced therapeutic effect as compared to administration of an oral solution or an inhalation formulation with a conventional inhalation device; (3) an enhanced lung deposition (deposited lung dose) as compared with a conventional inhalation device evidenced by scintigraphy or deconvolution, or derived from suitable in vitro indicators such as enhanced RD, RDDR, RF, and lower GSDs, as compared to administration with a conventional inhalation device; (4) reduced administration times, periods, and/or volumes as compared to administration with a conventional inhalation device; (5) a reduction in adverse side effects associated with oral formulations of a mast cell stabilizer, such as gastrointestinal irritation, or associated with conventional inhalation devices, such as cough; and (6) a longer duration of therapeutic effect as compared to administration of an oral solution or an inhaled formulation with a conventional inhalation device.

In some embodiments, the DD expressed as the percentage of the nominal dose of a mast cell stabilizer administered with a high efficiency nebulizer in the methods disclosed herein is at least about 30%, at least about 35%, at least about 40%, at least about 45%, at least about 50%, at least about 55%, at least about 60%, at least about 65%, about 65%, about 70%, about 30% to about 90%, about 40% to about 80%, about 45% to about 75%, about 50% to about 70%, about 30% to about 75%, about 40% to about 70%, about 45% to about 60%, or about 60% to about 70%.

TOR is the speed at which the liquid containing a mast cell stabilizer is administered from the inhalation device. In some embodiments, administration of the mast cell stabilizer with the high efficiency nebulizer provides a TOR of at least about 2 times, 3 times or 4 times the TOR achievable with a conventional inhalation device, such as a nebulizer. For example, in some embodiments the TOR is at least about at least about 150 mg/min, at least about 200 mg/min, at least about 250 mg/min, at least 300 mg/min, at least 350 mg/min, at least 400 mg/min, at least 500 mg/min, or from 200 to about 700 mg/min.

In some embodiments, use of a high efficiency nebulizer in the methods disclosed herein provides a RF (≤3.3 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In some embodiments, use of a high efficiency nebulizer in the methods disclosed herein provides a RF (≤3.3 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 40% to about 50%, about 35% to about 45%, about 35% to about 50%, about 30% to about 50%, about 44%, or about 36%.

In some embodiments, use of a high efficiency nebulizer in the methods disclosed herein provides a RF (1-5 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In some embodiments, use of a high efficiency nebulizer in the methods disclosed herein provides a RF (1-5 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%.

In some embodiments, use of a high efficiency nebulizer in the methods disclosed herein provides a RF (≤5 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, or about 75%. In some embodiments, use of a high efficiency nebulizer in the methods disclosed herein provides a RF (≤5 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, about 65% to about 75%, about 65% to about 80%, about 60% to about 80%, about 66%, or about 75%.

In some embodiments, use of a high efficiency nebulizer in the methods disclosed herein provides a RDDR of at least about 2 times, at least about 3 times or at least about 4 times the RDDR achievable with a conventional inhalation device. For example, where the mast cell stabilizer is cromolyn sodium, in some embodiments the RDDR is at least about 5 mg/min, at least about 10 mg/min, at least about 15 mg/min, at least about 20 mg/min, at least about 25 mg/min, at least about 30 mg/min, at least about 35 mg/min, at least about 40 mg/min, at least about 45 mg/min, at least about 50 mg/min, at least about 55 mg/min, or at least about 60 mg/min.

In some embodiments, administration of a mast cell stabilizer with a high efficiency nebulizer in the methods disclosed herein provides a GSD of emitted droplet size distribution of about 1.1 to about 2.1, about 1.2 to about 2.0, about 1.3 to about 1.9, less than about 2, at least about 1.4 to about 1.8, at least about 1.5 to about 1.7, about 1.4, about 1.5, about 1.6, or about 1.7. In some embodiments, administration of a mast cell stabilizer with a high efficiency nebulizer in the methods disclosed herein provides a MMAD of droplet size of about 1 μm to about 5 μm, about 2 to about 4 μm, about 3 to about 4 μm, about 3.5 to about 4.5 μm, or about 3.5 μm. In some particular embodiments, administration of a mast cell stabilizer in the methods disclosed herein provides droplets having a particular combination of MMAD and GSD, for example: an MMAD of less than about 5 μm and a GSD of about 1.1 to about 2.1; an MMAD of less than about 4.5 μm and a GSD of about 1.1 to about 2.1; an MMAD of about 1 μm to about 5 μm and a GSD of about 1.1 to about 2.1; an MMAD of about 1.5 to about 4.5 μm and a GSD of about 1.1 to about 2.1; an MMAD of less than about 5 μm and a GSD of about 1.1 to about 2.0; an MMAD of less than about 4.5 μm and a GSD of about 1.1 to about 2.0; an MMAD of about 1 μm to about 5 µm and a GSD of about 1.1 to about 2.0; an MMAD of about 1.5 to about 4.5 µm and a GSD of about 1.1 to about 2.0; an MMAD of less than about 5 µm and a GSD of about 1.1 to about 1.9; an MMAD of less than about 4.5 µm and a GSD of about 1.1 to about 1.9; an MMAD of about 1 µm to about 5 µm and a GSD of about 1.1 to about 1.9; an MMAD of about 1.5 to about 4.5 µm and a GSD of about 1.1 to about 1.9; an MMAD of less than about 5 µm and a GSD of about 1.1 to about 1.8; an MMAD of less than about 4.5 µm and a GSD of about 1.1 to about 1.8; an MMAD of about 1 µm to about 5 µm and a GSD of about 1.1 to about 1.8; an MMAD of about 1.5 to about 4.5 µm and a GSD of about 1.1 to about 1.8; an MMAD of about 3.5 µm or less and a GSD of about 1.7; an MMAD of about 4.1 µm or less and a GSD of about 1.7; an MMAD of about 3.5 µm and a GSD of about 1.7; or an MMAD of about 4.1 µm and a GSD of about 1.7.

In some embodiments, the median particle size of a mast cell stabilizer aerosol administered with a high efficiency nebulizer is between about 1 µm and about 6 µm, between about 2 µm and about 5 µm, between about 3 µm and about 5 µm, between about 3 µm and about 4 µm, about 1 µm, about 2 µm, about 3 µm, about 4 µm, about 5 µm, or about 6 µm. In some embodiments, the median particle size of cromolyn sodium aerosol administered with a high efficiency nebulizer is between about 1 µm and about 6 µm, between about 2 µm and about 5 µm, between about 3 µm and about 5 µm, between about 3 µm and about 4 µm, about 1 µm, about 2 µm, about 3 µm, about 4 µm, about 5 µm, or about 6 µm.

Inhalation Formulations

In some embodiments of the methods disclosed herein, inhalation formulations are administered by an inhalation device, e.g., a high efficiency nebulizer, to provide a systemically effective amount of a mast cell stabilizer for the treatment of a systemic mast cell related disorder. In some embodiments, the methods disclosed herein comprise administering a nominal dose of one or more mast cell stabilizers in an aqueous inhalation solution to the patient with an inhalation device, e.g., a high efficiency nebulizer.

In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments of the methods disclosed herein, an inhalation formulation administered with an inhalation device, e.g., a high efficiency nebulizer, produces in a human subject group an average $AUC_{(0-\infty)}$ of a mast cell stabilizer of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments of the methods disclosed herein, an inhalation formulation administered with an inhalation device, e.g., a high efficiency nebulizer, produces in a human subject group an average $C_{max}$ of a mast cell stabilizer greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments of the methods disclosed herein, an inhalation formulation administered with an inhalation device, e.g., a high efficiency nebulizer, produces in a human subject group an average $C_{max}$ of a mast cell stabilizer of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

In some embodiments of the methods disclosed herein, an inhalation formulation administered with an inhalation device, e.g., a high efficiency nebulizer, produces in a human subject group an average $C_{max}$ of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments of the methods disclosed herein, an inhalation formulation administered with an inhalation device, e.g., a high efficiency nebulizer, produces in a human subject group an average $C_{max}$ of cromolyn sodium of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 120 ng*hr/mL and/or an average $C_{max}$ of the mast cell stabilizer greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 120 ng*hr/mL and an average $C_{max}$ of the mast cell stabilizer greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 200 ng*hr/mL and an average $C_{max}$ of the mast cell stabilizer greater than about 80 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 330 ng*hr/mL and an average $C_{max}$ of the mast cell stabilizer greater than about 150 ng/mL. In some embodiments, of the methods disclosed herein, an inhalation formulation administered with an inhalation device, e.g., a high efficiency nebulizer, produces in a human subject group an average $AUC_{(0-\infty)}$ of a mast cell stabilizer greater than about 525 ng*hr/mL and an average $C_{max}$ of the mast cell stabilizer greater than about 230 ng/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 120 ng*hr/mL and/or an average $C_{max}$ of cromolyn sodium greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 120 ng*hr/mL and an average $C_{max}$ of cromolyn sodium greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 200 ng*hr/mL and an average $C_{max}$ of cromolyn sodium greater than about 80 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 330 ng*hr/mL and an average $C_{max}$ of cromolyn sodium greater than about 150 ng/mL. In some embodiments, of the methods disclosed herein, an inhalation formulation administered with an inhalation device, e.g., a high efficiency nebulizer, produces in a human subject group an average $AUC_{(0-\infty)}$ of cromolyn sodium greater than about 525 ng*hr/mL and an average $C_{max}$ of cromolyn sodium greater than about 230 ng/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 200 ng*hr/mL and an average $C_{max}$ of cromolyn sodium of about 80 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 330 ng*hr/mL and an average $C_{max}$ of cromolyn sodium of about 150 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 525 ng*hr/mL and an average $C_{max}$ of cromolyn sodium of about 230 ng/mL when a nominal dose of 80 mg of cromolyn sodium is administered with the inhalation device.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 180 ng*hr/mL to about 220 ng*hr/mL and an average $C_{max}$ of cromolyn sodium of about 70 ng/mL to about 90 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 300 ng*hr/mL to about 360 ng*hr/mL and an average $C_{max}$ of cromolyn sodium of about 135 ng/mL to about 165 ng/mL when a nominal dose of 40 mg of cromolyn sodium is administered with the inhalation device. In some embodiments, of the methods disclosed herein, an inhalation formulation administered with an inhalation device, e.g., a high efficiency nebulizer, produces in a human subject group an average $AUC_{(0-\infty)}$ of cromolyn sodium of about 475 ng*hr/mL to about 575 ng*hr/mL and an average $C_{max}$ of cromolyn sodium of about 200 ng/mL to about 260 ng/mL when a nominal dose of 80 mg of cromolyn sodium is administered with the inhalation device.

In some embodiments of the methods disclosed herein, an inhalation formulation administered with an inhalation device, e.g., a high efficiency nebulizer, provides mast cell stabilizer lung deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25 to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the mast cell stabilizer. In some embodiments of the methods disclosed herein, an inhalation formulation administered with an inhalation device, e.g., a high efficiency nebulizer, provides cromolyn sodium deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25 to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the cromolyn sodium.

In some embodiments of the methods disclosed herein, an inhalation formulation administered with an inhalation device, e.g., a high efficiency nebulizer, provides mast cell stabilizer lung deposition (deposited lung dose) of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the mast cell stabilizer. In some embodiments of the methods disclosed herein, an inhalation formulation administered with an inhalation device, e.g., a high efficiency nebulizer, provides cromolyn sodium lung deposition (deposited lung dose) of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the cromolyn sodium.

In some embodiments of the methods disclosed herein, an inhalation formulation administered with an inhalation device, e.g., a high efficiency nebulizer, provides mast cell stabilizer lung deposition (deposited lung dose) of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In some embodiments of the methods disclosed herein, an inhalation formulation administered with an inhalation device, e.g., a high efficiency nebulizer, provides mast cell stabilizer lung deposition (deposited lung dose) of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In some embodiments of the methods disclosed herein, an inhalation formulation administered with an inhalation device, e.g., a high efficiency nebulizer, provides cromolyn sodium lung deposition (deposited lung dose) of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In some embodiments of the methods disclosed herein, an inhalation formulation administered with an inhalation device, e.g., a high efficiency nebulizer, provides cromolyn sodium lung deposition (deposited lung dose) of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In some embodiments of the methods disclosed herein, an inhalation formulation containing a mast cell stabilizer is administered with an inhalation device, e.g., a high efficiency nebulizer, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In some embodiments of the methods disclosed herein, an inhalation formulation containing cromolyn sodium is administered with an inhalation device, e.g., a high efficiency nebulizer, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In some embodiments of the methods disclosed herein, a mast cell stabilizer is administered in an inhalation formulation with an inhalation device, e.g., a high efficiency nebulizer, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In some embodiments of the methods disclosed herein, cromolyn sodium is administered in an inhalation formulation with an inhalation device, e.g., a high efficiency nebulizer, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, an inhalation formulation administered with an inhalation device, e.g., a high efficiency nebulizer provides a bioavailability of a mast cell stabilizer of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, greater than about 50%, greater than about 55%, or greater than about 60% of the nominal dose. In some embodiments, an inhalation formulation administered with an inhalation device, e.g., a high efficiency nebulizer, in the methods disclosed herein provides a bioavailability of a mast cell stabilizer of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, or about 60% of the nominal dose.

In some embodiments of the methods disclosed herein, an inhalation formulation administered with an inhalation device, e.g., a high efficiency nebulizer provides a bioavailability of cromolyn sodium of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, or greater than about 50% of the nominal dose. In some embodiments, an aqueous inhalation formulation administered with an inhalation device, e.g., a high efficiency nebulizer, in the methods disclosed herein provides a bioavailability of cromolyn sodium of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, or about 50% of the nominal dose.

In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of the mast cell stabilizer greater than about 120 ng*hr/mL, and/or an average $C_{max}$ of the mast cell stabilizer greater than about 55 ng/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of the mast cell stabilizer greater than about 120 ng*hr/mL and an average $C_{max}$ of the mast cell stabilizer greater than about 55 ng/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of the mast cell stabilizer greater than about 200 ng*hr/mL, and an average $C_{max}$ of the mast cell stabilizer greater than about 80 ng/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of the mast cell stabilizer greater than about 330 ng*hr/mL and an average $C_{max}$ of the mast cell stabilizer greater than about 150 ng/mL. In some embodiments, of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of the mast cell stabilizer greater than about 525 ng*hr/mL and an average $C_{max}$ of the mast cell stabilizer greater than about 230 ng/mL.

In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 120 ng*hr/mL and/or an average $C_{max}$ of cromolyn sodium greater than about 55 ng/mL. In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 120 ng*hr/mL and an average $C_{max}$ of cromolyn sodium greater than about 55 ng/mL. In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 200 ng*hr/mL and an average $C_{max}$ of cromolyn sodium greater than about 80 ng/mL. In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 330 ng*hr/mL and an average $C_{max}$ of cromolyn sodium greater than about 150 ng/mL. In some embodiments, of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 525 ng*hr/mL and an average $C_{max}$ of cromolyn sodium greater than about 230 ng/mL.

In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of a mast cell stabilizer greater than about 120 ng*hr/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of a mast cell stabilizer greater than about 200 ng*hr/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of a mast cell stabilizer greater than about 330 ng*hr/mL. In some embodiments of the methods disclosed herein, an inhalation formulation administered with an inhalation device, e.g., a high efficiency nebulizer, provides a bioavailability of a mast cell stabilizer greater than about 5% and produces in a human subject group an average $AUC_{(0-\infty)}$ of a mast cell stabilizer greater than about 525 ng*hr/mL.

In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 120 ng*hr/mL. In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 200 ng*hr/mL. In some embodiments of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 330 ng*hr/mL. In some embodiments, of the methods disclosed herein, an inhalation formulation administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 525 ng*hr/mL.

In some embodiments of the methods disclosed herein, an inhalation formulation comprising 40 mg cromolyn sodium administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 200 ng*hr/mL. In some embodiments of the methods disclosed herein, an inhalation formulation comprising 40 mg cromolyn sodium administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 330 ng*hr/mL. In some embodiments, of the methods disclosed herein, an inhalation formulation comprising 80 mg cromolyn sodium administered with an inhalation device, e.g., a high efficiency nebulizer, provides a bioavailability of cromolyn sodium greater than about 5% and produces in a human subject group an average $AUC_{(0-\infty)}$ of cromolyn sodium greater than about 525 ng*hr/mL.

In some embodiments of the methods disclosed herein, an inhalation formulation administered with an inhalation device, e.g., a high efficiency nebulizer, has an RF (≤3.3 μm) of at least about 30% and produces in a human subject group an average $AUC_{(0-\infty)}$ of a mast cell stabilizer greater than about 120 ng*hr/mL. In some embodiments of the methods disclosed herein, an inhalation formulation administered with an inhalation device, e.g., a high efficiency nebulizer, has an RF (≤3.3 μm) of at least about 30% and produces in a human subject group an average $AUC_{(0-\infty)}$ of a mast cell stabilizer greater than about 200 ng*hr/mL. In some embodiments of the methods disclosed herein, an inhalation formulation administered with an inhalation device, e.g., a high efficiency nebulizer, has an RF (≤3.3 μm) of at least about 40% and produces in a human subject group an average $AUC_{(0-\infty)}$ of a mast cell stabilizer greater than about 330 ng*hr/mL. In some embodiments, of the methods disclosed herein, an inhalation formulation administered with an inhalation device, e.g., a high efficiency nebulizer, has an RF (≤3.3 μm) of at least about 40% and produces in a human subject group an average $AUC_{(0-\infty)}$ of a mast cell stabilizer greater than about 525 ng*hr/mL.

In some embodiments of the methods disclosed herein, an inhalation formulation administered with an inhalation device, e.g., a high efficiency nebulizer, has an RF (≤3.3 μm) of at least about 30% and produces in a human subject group an average $AUC_{(0-\infty)}$ of cromolyn sodium greater than about 120 ng*hr/mL. In some embodiments of the methods disclosed herein, an inhalation formulation administered with an inhalation device, e.g., a high efficiency nebulizer, has an RF (≤3.3 μm) of at least about 30% and produces in a human subject group an average $AUC_{(0-\infty)}$ of cromolyn sodium greater than about 200 ng*hr/mL. In some embodiments of the methods disclosed herein, an inhalation formulation administered with an inhalation device, e.g., a high efficiency nebulizer, has an RF (≤3.3 μm) of at least about 40% and produces in a human subject group an average $AUC_{(0-\infty)}$ of cromolyn sodium greater than about 330 ng*hr/mL. In some embodiments, of the methods disclosed herein, an inhalation formulation administered with an inhalation device, e.g., a high efficiency nebulizer, has an RF (≤3.3 μm) of at least about 40% and produces in a human subject group an average $AUC_{(0-\infty)}$ of cromolyn sodium greater than about 525 ng*hr/mL.

In some embodiments of the methods disclosed herein, an inhalation formulation comprising 40 mg cromolyn sodium administered with an inhalation device, e.g., a high efficiency nebulizer, has an RF (≤3.3 μm) of at least about 30% and produces in a human subject group an average $AUC_{(0-\infty)}$ of cromolyn sodium greater than about 200 ng*hr/mL. In some embodiments of the methods disclosed herein, an inhalation formulation comprising 40 mg cromolyn sodium administered with an inhalation device, e.g., a high efficiency nebulizer, has an RF (≤3.3 μm) of at least about 40% and produces in a human subject group an average $AUC_{(0-\infty)}$ of cromolyn sodium greater than about 330 ng*hr/mL. In some embodiments of the methods disclosed herein, an inhalation formulation comprising 80 mg cromolyn sodium administered with an inhalation device, e.g., a high efficiency nebulizer, has an RF (≤3.3 μm) of at least about 40% and produces in a human subject group an average $AUC_{(0-\infty)}$ of cromolyn sodium greater than about 525 ng*hr/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 8.5 ng*hr/mL and an average $C_{max}$ of cromolyn sodium of about 3.9 ng/mL per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 6.6 ng*hr/mL and an average $C_{max}$ of cromolyn sodium of about 3.0 ng/mL, per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 5.3 ng*hr/mL and an average $C_{max}$ of cromolyn sodium of about 2.2 ng/mL per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of from about 5.3 ng*hr/mL to about 8.5 ng*hr/mL and an average $C_{max}$ of cromolyn sodium of about 2.2 ng/mL to about 3.9 ng/mL per mg of cromolyn sodium administered with the inhalation device when the nominal dose of cromolyn sodium administered is in the range of about 40 mg to about 80 mg.

In some embodiments of the methods disclosed herein, an inhalation formulation containing a mast cell stabilizer such as cromolyn sodium is administered with an inhalation device, e.g., a high efficiency nebulizer, at a fill volume of less than about 0.25 mL, less than about 0.5 mL, at least about 0.5 mL to about 1.5 mL, at least about 0.5 mL to about 1.8 mL, at least about 1.5 mL, or at least about 2.0 mL. In some embodiments, an inhalation formulation is administered with an inhalation device, e.g., a high efficiency nebulizer, at a fill volume about 0.1 mL to about 5.0 mL, about 0.25 mL to about 2.0 mL, about 0.5 mL to about 1.8 mL, about 0.5 mL to about 2 mL, about 0.5 mL to about 1.5 mL, about 0.5 mL to about 1.0 mL, about 0.5 mL or less, about 1 mL or less, about 1.5 mL or less, about 2.0 mL or less, about 2.5 mL or less, about 3.0 mL or less, about 3.5 mL or less, about 4.0 mL or less, about 4.5 mL or less, or about 5.0 mL or less. In some embodiments, an inhalation formulation is administered with an inhalation device, e.g., a high efficiency nebulizer, at a fill volume of about 0.5 mL, about 1.0 mL, about 1.5 mL, about 1.8 mL, about 2.0 mL, about 2.5 mL, about 3.0 mL, about 3.5 mL, about 4.0 mL, about 4.5 mL, or about 5.0 mL. In some embodiments, an inhalation formulation is administered with an inhalation device, e.g., a high efficiency nebulizer, which provides for a residual volume of mast cell stabilizer after administration of the mast cell stabilizer of less than about 10%, less than about 5%, or less than about 3% of the nominal dose.

In some embodiments of the methods disclosed herein, an inhalation formulation containing a mast cell stabilizer is administered with an inhalation device, e.g., a high efficiency nebulizer, wherein the concentration of the mast cell stabilizer is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight. In some embodiments of the methods disclosed herein, an inhalation formulation containing a mast cell stabilizer is administered with an inhalation device, e.g., a high efficiency nebulizer, wherein the concentration of the mast cell stabilizer is from about 1% by weight to about 10% by weight, from about 2% by weight to about 8% by weight, from about 2% by weight to about 6% by weight, or from about 3% by weight to about 5% by weight. In some embodiments of the methods disclosed herein, an inhalation formulation containing a mast cell stabilizer is administered with an inhalation device, e.g., a high efficiency nebulizer, wherein the concentration of the mast cell stabilizer is about 1% by weight, about 2% by weight, about 3% by weight, about 4% by weight, about 5% by weight, about 6% by weight, about 7% by weight, about 8% by weight, about 9% by weight, or about 10% by weight.

In some embodiments of the methods disclosed herein, an inhalation formulation containing cromolyn sodium is administered with an inhalation device, e.g., a high efficiency nebulizer, wherein the concentration of the cromolyn sodium is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight.

In some embodiments of the methods disclosed herein, an inhalation formulation containing cromolyn sodium is administered with an inhalation device, e.g., a high efficiency nebulizer, wherein the concentration of the cromolyn sodium is from about 1% by weight to about 10% by weight, from about 2% by weight to about 8% by weight, from about 2% by weight to about 6% by weight, or from about 3% by weight to about 5% by weight. In some embodiments of the methods disclosed herein, an inhalation formulation containing cromolyn sodium is administered with an inhalation device, e.g., a high efficiency nebulizer, wherein the concentration of the cromolyn sodium is about 1% by weight, about 2% by weight, about 3% by weight, about 4% by weight, about 5% by weight, about 6% by weight, about 7% by weight, about 8% by weight, about 9% by weight, or about 10% by weight.

In some embodiments, an inhalation formulation containing a mast cell stabilizer is administered with an inhalation device, e.g., a high efficiency nebulizer, in about 0.25 to about 10 minutes, about 0.50 to about 8 minutes, less than about 8 minutes, less than about 7 minutes, less than about 6 minutes, less than about 5 minutes, less than about 4 minutes, less than about 3 minutes, less than about 2 minutes, less than about 1.8 minutes, less than about 1.5 minutes, or less than 1 minute. In some embodiments, the inhalation formulation is administered in about 3 minutes or less. In some embodiments, the inhalation formulation is administered in about 1 minute, about 2 minutes, about 3 minutes, about 4 minutes, about 5 minutes, about 6 minutes, about 7 minutes, about 8 minutes, about 9 minutes, or about 10 minutes.

In some embodiments of the methods disclosed herein, administration of a mast cell stabilizer with a high efficiency nebulizer provides at least about a 1.5-fold, at least about a 1.8-fold, at least about a two-fold, at least about a three-fold, at least about a four-fold, or at least about a five-fold increase in one or more of $AUC_{last}$, $AUC_{(0-\infty)}$, or $C_{max}$ as compared to the same or lower nominal dose of the mast cell stabilizer administered with a conventional inhalation device or an oral formulation, e.g., a liquid oral formulation, tablet, or capsule.

In some embodiments of the methods disclosed herein, inhalation formulations administered with a high efficiency nebulizer are substantially free of a preservative, such as benzyl alcohol. In some embodiments of the methods disclosed herein, inhalation formulations administered with a high efficiency nebulizer further comprise at least one excipient. In some embodiments, the excipient is selected from the group consisting of stabilizers and antioxidants (such as citric acid, ascorbic acid, ethylenediamine tetra acetic acid (EDTA), sodium metabisulfite, or a salt of any thereof), an osmolarity adjusting agent (such as sodium chloride, mannitol, or sorbitol), a surfactant (such as polysorbate 80, vitamin E, tocopherol polyethylene glycol, and Tyloxapol), or a pH buffer.

In some embodiments of the methods disclosed herein, inhalation formulations administered with an inhalation device, e.g., a high efficiency nebulizer, are hypotonic. In some embodiments of the methods disclosed herein, inhalation formulations administered with an inhalation device, e.g., a high efficiency nebulizer, are sub-isotonic. In some embodiments of the methods disclosed herein, inhalation formulations administered with an inhalation device, e.g., a high efficiency nebulizer, have an osmolality greater than about 70 mOsm/kg. In some embodiments of the methods disclosed herein, inhalation formulations administered with an inhalation device, e.g., high efficiency nebulizer, have an osmolality of at least about 100 mOsm/kg. In some embodiments of the methods disclosed herein, inhalation formulations administered with an inhalation device, e.g., high efficiency nebulizer, have an osmolality of at least about 150 mOsm/kg.

Combination Therapies

In some embodiments of the methods disclosed herein, one or more different formulations of mast cell stabilizers are co-administered by different routes of administration to provide systemically effective amounts of the mast cell stabilizers. For example, in some embodiments, a composition comprising a mast cell stabilizer, e.g., cromolyn sodium, is administered with a dry powder inhaler and a different composition comprising a mast cell stabilizer, e.g., cromolyn sodium, is co-administered in a liquid oral formulation to treat a systemic mast cell related disorder. In some embodiments, a composition comprising a mast cell stabilizer, e.g., cromolyn sodium, is administered with a dry powder inhaler and a different composition comprising a mast cell stabilizer, e.g., cromolyn sodium, is co-administered in a solid oral formulation, e.g., a capsule or tablet, to treat a systemic mast cell related disorder. In some embodiments, a composition comprising a mast cell stabilizer, e.g., cromolyn sodium, is administered with a metered dose inhaler and a different composition comprising a mast cell stabilizer, e.g., cromolyn sodium, is co-administered in a liquid oral formulation to treat a systemic mast cell related disorder. In some embodiments, a composition comprising a mast cell stabilizer, e.g., cromolyn sodium, is administered with a metered dose inhaler and a different composition comprising a mast cell stabilizer, e.g., cromolyn sodium, is co-administered in a solid oral formulation, e.g., a tablet or capsule, to treat a systemic mast cell related disorder. In some embodiments, a composition comprising a mast cell stabilizer, e.g., cromolyn sodium, is administered with a dry powder inhaler and a different composition comprising a mast cell stabilizer, e.g., cromolyn sodium, is co-administered with a metered dose inhaler to treat a systemic mast cell related disorder. In some embodiments, a composition comprising a mast cell stabilizer, e.g., cromolyn sodium, is administered with a dry powder inhaler and a different composition comprising a mast cell stabilizer, e.g., cromolyn sodium, is co-administered with a metered dose inhaler to treat a systemic mast cell related disorder. In some embodiments, a composition comprising a mast cell stabilizer, e.g., cromolyn sodium, is administered with a high efficiency nebulizer and a different composition comprising a mast cell stabilizer, e.g., cromolyn sodium, is co-administered in a liquid oral formulation to treat a systemic mast cell related disorder. In some embodiments, a composition comprising a mast cell stabilizer, e.g., cromolyn sodium, is administered with a high efficiency nebulizer and a different composition comprising a mast cell stabilizer, e.g., cromolyn sodium, is co-administered in a solid oral formulation, e.g., a tablet or capsule, to treat a systemic mast cell related disorder. In some embodiments, a composition comprising a mast cell stabilizer, e.g., cromolyn sodium, is administered with a jet nebulizer and a different composition comprising a mast cell stabilizer, e.g., cromolyn sodium, is co-administered in a liquid oral formulation to treat a systemic mast cell related disorder. In some embodiments, a composition comprising a mast cell stabilizer, e.g., cromolyn sodium, is administered with a jet nebulizer and a different composition comprising a mast cell stabilizer, e.g., cromolyn sodium, is co-administered in a solid oral formulation, e.g., a tablet or capsule, to treat a systemic mast cell related disorder.

EXAMPLES

The examples below describe some embodiments of the methods described herein. Methods and materials that are not specifically described in the following examples are within the scope of the invention and will be apparent to those skilled in the art with reference to the disclosure herein.

Example 1

Formulations

The formulations described in Table 1 are prepared as follows: The composition ingredients are added sequentially to a glass beaker with a magnet stirrer and about 90 g of purified water in the order listed in Table 1, ensuring that each ingredient is dissolved before the next is added. The weight is then adjusted to 100.0 g by adding additional purified water. The resulting solutions are then sterilized by filtration through 0.2-0.22 μm sterile filters, and 0.5 to 5 mL aliquots are added to pre-sterilized glass or sterile polyethylene or polypropylene blow fill and seal vials by a standard blow fill and seal procedure. Alternative sterilization methods may be applied using heat sterilization in an autoclave.

TABLE 1

| | Formulation No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Cromolyn sodium (DSCG) (wt %) | 2.0 | 3.0 | 4.0 | 4.0 | 4.0 | 4.0 | 4.0 | 5.0 | 6.0 | 3.0 | 3.0 | 3.0 | 3.0 |
| NaCl (wt %) | 0.7 | 0.5 | 0.3 | 0.25 | 0.2 | 0.2 | 0.2 | 0.15 | 0.1 | 0.2 | 0.3 | 0.4 | 0.5 |
| Mannitol (wt %) | 0.4 | 0.8 | 1.0 | 1.1 | 1.2 | 1.25 | 1.25 | 1.4 | 1.5 | | | | |
| EDTA-Na (wt %) | 0.01 | 0.02 | 0.03 | 0.01 | 0.02 | 0.03 | 0.02 | 0.03 | 0.04 | 0.01 | 0.02 | 0.03 | 0.04 |
| Hyaluronic acid (wt %) | | | 0.25 | 0.5 | 1.0 | | | | | | 0.25 | 0.5 | 1.0 |
| Propylene glycol (wt %) | | | | | | | | | | 1.0 | 2.0 | 3.0 | 4.0 |
| Purified Water (wt %) | 96.9 | 95.7 | 94.4 | 94.1 | 93.6 | 94.5 | 94.5 | 93.4 | 92.4 | 95.8 | 94.4 | 93.1 | 91.5 |

Example 2

Characterization of Aerosols Produced with a High Efficiency Nebulizer

The MMAD, GSD, DD, and RF of a representative inhaled cromolyn sodium formulation (PA-101) delivered via a high efficiency nebulizer (eFlow®, PARI, 30L) were determined as described in USP<1601>. The values determined were: MMAD=3.5 μm; GSD=1.7; DD=68%; RF (≤5 μm)=75%; and RF (≤3.3 μm)=44%.

The MMAD, GSD, and RF of a representative inhaled cromolyn sodium formulation (PA-101) delivered via a high efficiency nebulizer (eFlow®, PARI, 40L) were determined as described in USP<1601>. The values determined were: MMAD=4.1 μm; GSD=1.7; RF 5 μm)=66%; and RF 3.3 μm)=36%.

Example 3

Single-Dose, Dose Escalation Study

Objectives:
The objectives of the study are as follows:
Primary:
Part 1: To determine the systemic availability and pharmacokinetic (PK) profile of single doses of a representative inhaled cromolyn sodium formulation (PA-101) delivered via a high efficiency nebulizer (eFlow®, PARI) using two different aerosol membranes (30L and 40L) in comparison with marketed formulations of cromolyn sodium (oral solution and an inhalation aerosol) in healthy subjects.

Part 2: To assess the pharmacokinetic profile of PA-101 administered as single day three times daily dosing via a high efficiency nebulizer (eFlow®, PARI) in comparison with marketed formulations of cromolyn sodium (oral solution and inhalation aerosol) administered as single day TID dosing in patients with systemic mastocytosis.

Secondary:
To assess the safety and tolerability of PA-101 in comparison with marketed formulations of cromolyn sodium (oral solution and an inhalation aerosol).

Methodology:
This was a Phase 1, randomized, open-label, single-centre, dose-ranging, cross-over study conducted in two parts in total of 18 subjects. Part 1 was conducted in total of 12 healthy adult subjects of 18-45 years of age. Part 2 was conducted in a total of 5 adult patients of 18-45 years of age with systemic mastocytosis. Parts 1 and 2 were conducted in parallel.

Study Treatments, Dose and Mode of Administration:
Part 1:
1. 40 mg PA-101 (4% DSCG, 40 mg/1 mL), oral inhalation via eFlow 30L.
2. 80 mg PA-101 (4% DSCG, 80 mg/2 mL), oral inhalation via eFlow 30L.
3. 40 mg PA-101 (4% DSCG, 40 mg/1 mL), oral inhalation via eFlow 40L.
4. 20 mg cromolyn sodium inhalation aerosol (1% DSCG, 20 mg/2 mL) (commercially available product), oral inhalation via LC Plus.
5. 200 mg oral sodium cromoglycate solution (commercially available product), oral administration.

Part 2:
1. 40 mg PA-101 (4% DSCG 40 mg/1 mL), oral inhalation via eFlow 30L
2. 200 mg oral sodium cromoglycate solution (commercially available product), oral administration.

In Part 1, all study subjects received each study treatment in the morning (at 8:00 am, +/−30 minutes) as a single dose treatment. Prior to each dosing day, subjects were admitted to the clinic in the morning for baseline (pre-dose) assessments. Subjects were required to remain in the clinic for 12 h after study drug administration on each dosing day. Treatment Visits were separated by a washout period of 2 to 5 days.

In Part 2, all study subjects received each study treatment three times daily (TID) (at 08:00 am, 14:00 μm and 20:00 μm, +/−30 minutes) as a single day treatment. Prior to each dosing day, subjects were admitted to the clinic in the morning for baseline (pre-dose) assessments. Subjects were required to remain in the clinic for 24 h after study drug administration on each dosing day.

The main delivery device for administering PA-101 was the open system eFlow nebulizer using the 30L aerosol head, which generates aerosol particles with a median size of about 3.0 μm. The 40L aerosol head (generating aerosol particles with a median size of about 4.0 μm) was tested as a comparator arm in Part 1 only.

Duration of Study:

The duration of both Parts 1 and 2 of the study was one day.

Criteria for Evaluation:

Pharmacokinetic measurements: The PK parameters evaluated for plasma cromolyn sodium (DSCG) were maximum concentration ($C_{max}$), time to maximum concentration ($T_{max}$), terminal elimination half-life ($T_{1/2}$), area under the plasma concentration-time curve from time=0 to time of last measurable drug concentration ($AUC_{0-t}$), and area under the plasma concentration-time curve from time=0 to infinity ($AUC_{0-\infty}$). Urine DSCG levels were measured for total DSCG excretion in the urine, and the bioavailability of the DSCG was calculated from the measured levels.

Safety measurements: Adverse events including gastrointestinal disturbance (e.g., abdominal pain, nausea, vomiting), changes in vital signs, 12-lead ECG and clinical laboratory tests (hematology, chemistry and urinalysis).

Statistical Measurements:

Pharmacokinetic parameters and plasma concentrations are listed and summarized. The summary statistics are presented as the geometric mean, arithmetic mean, arithmetic standard deviation (SD), min, median, max and n. The geometric statistics are not presented for $T_{max}$. Analysis of variance (ANOVA) including terms for subject and treatment are used to calculate point estimates, and confidence intervals (CI) for treatment differences with respect to PK parameters (90% CT) are calculated.

The incidence of AEs was compared between treatment groups. Summary tables and individual subject listings are provided for all safety measurements and the results are presented by treatment group. Descriptive statistics are used to summarise data where appropriate.

Results:

The pharmacokinetic parameters measured in the single dose study (Part 1) are shown in the following table:

TABLE 2

| PK parameter | Oral solution, 200 mg | Inhalation aerosol, 20 mg | PA-101 (40L), 40 mg | PA-101 (30L), 40 mg | PA-101 (30L), 80 mg | Ratio (PA-101 (30L; 40 mg))/(oral solution (200 mg)) | Ratio (PA-101 (30L; 40 mg)/(inhalation aerosol (20 mg)) |
|---|---|---|---|---|---|---|---|
| $C_{max}$ (ng/mL) | 5.2 (±3.1) | 17.8 (±10.4) | 88.6 (±45.5) | 156 (±104) | 236 (±124) | x30 | x8.8 |
| $T_{max}$ (h) | 3.2 (±2.1) | 0.6 (±0.1) | 0.6 (±0.1) | 0.7 (±0.1) | 0.7 (±0.1) | | |
| $AUC_{0-t}$ (h * ng/mL) | 29.4 (±10.4) | 39.1 (±15.1) | 206 (±94.3) | 329 (±144) | 514 (±186) | x11 | x8.4 |
| $AUC_{(0-\infty)}$ (h * ng/mL) | 33.3 (±11.7) | 40.6 (±15.6) | 212 (±96.0) | 338 (±146) | 526 (±198) | | |
| $T_{1/2}$ (h) | 4.3 (±1.3) | 2.5 (±0.8) | 2.5 (±0.7) | 2.2 (±0.6) | 2.1 (±0.5) | | |
| Bioavailability (%) | 0.6 | 6.5 | 16.3 | 25.0 | 22.7 | X42 | X3.8 |

Values shown in parentheses are (±SD).

Modeling of lung deposition with an aerosol from the 30L and 40L devices using the Finlay model (Finlay, W H, and A R Martin, "Recent advances in predictive understanding respiratory tract deposition", Journal of Aerosol Medicine, Vol 21:189-205 (2008)) indicated that the lung deposition with the two devices should be very similar. However, the AUC value obtained with 40 mg dose using the 30L device (338 ng*hr/mL) was surprisingly high compared to the value (212 ng*hr/mL) from the 40L device. Cromlyn sodium is not metabolized in the body and is excreted intact via bile and urine. Cromolyn sodium deposited in the lung during inhalation will appear in the plasma, and the AUC would therefore be a surrogate for cromolyn sodium deposited in the lung. Any cromolyn sodium swallowed during inhalation will contribute negligibly to the AUC since the oral bioavailability of cromolyn is only about 1% (Richards et al, J Pharmacol Exp Ther, Vol. 241, No. 3: 1028-1032 (1987)). The AUC data therefore indicate that at the same dose (40 mg), the lung deposition with the 30L device was surprisingly higher than that with the 40L device.

The numbers of adverse events observed in the single dose study (Part 1) are shown in the following table:

TABLE 3

| Adverse Event | Placebo | PA-101 (40L), 40 mg | PA-101 (30L), 40 mg | PA-101 (30L), 80 mg | Inhalation aerosol, 20 mg | Oral solution, 200 mg |
|---|---|---|---|---|---|---|
| Cough | 1 | 1 | — | 1 | 1 | — |
| Oropharyngeal pain | — | — | — | — | 1 | 1 |
| Rhinorrhoea | 1 | — | — | — | — | — |
| Dizziness | — | — | 2 | — | — | — |
| Headache | — | — | — | 1 | — | 1 |
| Dysgeusia | — | — | — | — | — | 1 |
| Somnolence | — | — | — | 1 | — | — |
| Catheter-site Reaction | — | — | 1 | — | — | 1 |
| Nasopharygitis | — | — | — | — | 1 | — |
| Sinusitis | — | — | — | 1 | — | — |
| Abdominal Discomfort | — | — | — | — | — | 1 |
| Increased Appetite | — | 1 | — | — | — | — |

Example 4

Efficacy Study

Objective

The objectives of the study are: to determine the efficacy profile of cromolyn sodium inhalation formulation when administered using a high efficiency nebulizer in comparison with oral formulation of cromolyn sodium in patients with systemic mastocytosis; to assess the safety and tolerability of cromolyn sodium inhalation formulation when administered using a high efficiency nebulizer; to compare the pharmacokinetic profile of cromolyn sodium inhalation formulation when administered using a high efficiency nebulizer in comparison with oral formulation of cromolyn sodium in patients with indolent systemic mastocytosis.

Methodology

This is a Phase 2, randomized, double-blind, active-controlled, parallel arm, efficacy study in patients with indolent systemic mastocytosis.

At least about thirty six (36) adult human systemic mastocytosis patients are randomized to one of three treatment groups: (1) cromolyn sodium inhalation formulation administered thrice daily with a high efficiency nebulizer; (2) placebo formulation administered three times daily with a high efficiency nebulizer; and, (3) oral formulation of cromolyn sodium administered four times daily.

Following the Screening Visit (SV), eligible subjects enter a 4-week Washout/Baseline Period for daily assessment of baseline symptoms using a diary and to washout cromolyn sodium in oral cromolyn sodium users. At the end of the Washout Period, eligible subjects are randomized to receive cromolyn sodium inhalation formulation using a high efficiency nebulizer or oral cromolyn sodium formulation or placebo for 6 weeks.

The main criteria for inclusion are: a) Indolent systemic mastocytosis patients uncontrolled with antihistaminic therapy; b) 18-65 years of age; c) mastocytosis diagnosis confirmed by positive bone marrow biopsy; d) no recent systemic corticosteroid or immunosuppressive therapy; c) no history of cancer except basal cell carcinoma; and, f) no concurrent uncontrolled disease.

Criteria for Evaluation:

The primary efficacy variable is significant improvement in clinical symptoms at the end of treatment period following treatment with cromolyn sodium inhalation formulation when administered using a high efficiency nebulizer in comparison with oral formulation of cromolyn sodium.

The PK parameters evaluated for plasma cromolyn sodium are maximum concentration ($C_{max}$), time to maximum concentration ($T_{max}$), terminal elimination half-life ($T_{1/2}$), area under the plasma concentration-time curve from time=0 to time of last measurable drug concentration ($AUC_{0-t}$), and area under the plasma concentration-time curve from time=0 to infinity ($AUC_{0-\infty}$).

The safety parameters include adverse events (AEs) including assessment of gastrointestinal disturbance (e.g., abdominal pain, nausea, vomiting), and changes in vital signs and clinical laboratory tests.

Results:

At the end of the treatment period, patients exhibit a significant improvement in clinical symptoms with minimal AEs as compared to placebo and the oral formulation of cromolyn sodium.

What is claimed is:

1. A method of treating an inflammatory disorder in a patient, comprising administering to said patient a therapeutically effective amount of cromolyn sodium utilizing a dosage form comprising:
    (a) an aqueous pharmaceutical composition comprising (i) from about 2% to about 6% by weight of cromolyn sodium, and (ii) an osmolarity adjusting agent consisting of (A) between about 0.1% to about 0.5% by weight of sodium chloride, inclusive of the endpoints, and (B) optionally salts of EDTA; and
    (b) an inhalation device that forms an aerosol of said pharmaceutical composition, said aerosol exhibiting a respirable fraction of said pharmaceutical composition (≤5 μm) as measured by USP <1601>of at least about 60%.

2. The method of claim 1, wherein said salts of EDTA comprise sodium EDTA.

3. The method of claim 1, wherein said pharmaceutical composition comprises from about 5 mg to about 80 mg of cromolyn sodium.

4. The method of claim 1, wherein said pharmaceutical composition comprises from about 36 mg to about 44 mg of cromolyn sodium.

5. The method of claim 1, wherein said aerosol has a respirable fraction (≤3.3 μm) as measured by USP <1601>of at least about 30%.

6. The method of claim 1, wherein said aerosol has a respirable fraction (≤3.3 μm) as measured by USP <1601>of at least about 30% and a respirable fraction (≤5 μm) as measured by USP <1601>of at least about 75%.

7. The method of claim 1, wherein said sodium chloride is at a concentration of between 0.1% to 0.2% by weight, inclusive of the endpoints.

8. The method of claim 1, wherein said osmolarity adjusting agent consists of between 0.1% to 0.2% by weight of sodium chloride, inclusive of the endpoints, and sodium EDTA.

9. The method of claim 1, wherein said pharmaceutical composition comprises from about 4% to about 6% by weight of cromolyn sodium.

10. The method of claim 9, wherein said osmolarity adjusting agent consists of between 0.1% to 0.2% by weight of sodium chloride, inclusive of the endpoints, and sodium EDTA.

11. A method of treating fibrosis in a patient, comprising administering to said patient a therapeutically effective amount of cromolyn sodium utilizing a dosage form comprising:
    (a) an aqueous pharmaceutical composition comprising (i) from about 2% to about 6% by weight of cromolyn sodium, and (ii) an osmolarity adjusting agent consisting of (A) between about 0.1% to about 0.5% by weight of sodium chloride, inclusive of the endpoints, and (B) optionally salts of EDTA; and
    (b) an inhalation device that forms an aerosol of said pharmaceutical composition, said aerosol exhibiting a respirable fraction of said pharmaceutical composition (≤5 μm) as measured by USP <1601>of at least about 60%.

12. The method of claim 11, wherein said salts of EDTA comprise sodium EDTA.

13. The method of claim 11, wherein said pharmaceutical composition comprises from about 5 mg to about 80 mg of cromolyn sodium.

14. The method of claim 11, wherein said pharmaceutical composition comprises from about 36 mg to about 44 mg of cromolyn sodium.

15. The method of claim 11, wherein said aerosol has a respirable fraction (≤3.3 μm) as measured by USP <1601> of at least about 30%.

16. The method of claim 11, wherein said aerosol has a respirable fraction (≤3.3 μtm) as measured by USP <1601> of at least about 30% and a respirable fraction (≤5 μtm) as measured by USP <1601> of at least about 75%.

17. The method of claim 11, wherein said sodium chloride is at a concentration of between 0.1% to 0.2% by weight, inclusive of the endpoints.

18. The method of claim 11, wherein said osmolarity adjusting agent consists of between 0.1% to 0.2% by weight of sodium chloride, inclusive of the endpoints, and sodium EDTA.

19. The method of claim 11, wherein said pharmaceutical composition comprises from about 4% to about 6% by weight of cromolyn sodium.

20. The method of claim 19, wherein said osmolarity adjusting agent consists of between 0.1% to 0.2% by weight of sodium chloride, inclusive of the endpoints, and sodium EDTA.

21. The method of claim 11, wherein the fibrosis is Kidney fibrosis.

22. The method of claim 11, wherein the fibrosis is Hepatic fibrosis.

* * * * *